United States Patent
Alton et al.

(10) Patent No.: US 6,936,695 B1
(45) Date of Patent: Aug. 30, 2005

(54) MANUFACTURE AND EXPRESSION OF LARGE STRUCTURAL GENES

(75) Inventors: Norman K. Alton, Thousand Oaks, CA (US); Mary A. Peters, Boulder, CO (US); Yitzhak Stabinsky, Boulder, CO (US); David L. Snitman, Boulder, CO (US)

(73) Assignee: Intermune, Inc., Brisbane, CA (US)

( * ) Notice: Subject to any disclaimer, the term of this patent is extended or adjusted under 35 U.S.C. 154(b) by 0 days.

(21) Appl. No.: 08/462,022

(22) Filed: Jun. 5, 1995

Related U.S. Application Data

(63) Continuation of application No. 06/483,451, filed on Apr. 15, 1983, which is a continuation-in-part of application No. 06/375,494, filed on May 6, 1982, now abandoned.

(51) Int. Cl.$^7$ .......................... C07K 17/00; C12P 21/04
(52) U.S. Cl. .................................... 530/351; 435/69.51
(58) Field of Search ........................ 435/69.51; 530/351

(56) References Cited

U.S. PATENT DOCUMENTS

| | | | |
|---|---|---|---|
| 4,237,224 A | 12/1980 | Cohen et al. | 435/69.1 |
| 4,264,731 A | 4/1981 | Shine | 435/91.41 |
| 4,273,875 A | 6/1981 | Manis | 435/91.4 |
| 4,293,652 A | 10/1981 | Cohen | 435/69.1 |
| 4,332,892 A | 6/1982 | Ptashne et al. | 435/69.7 |
| 4,338,397 A | 7/1982 | Gilbert et al. | 435/69.1 |
| 4,342,832 A | 8/1982 | Goeddel et al. | 435/91.41 |
| 4,349,629 A | 9/1982 | Carey et al. | 435/69.1 |
| 4,366,246 A | 12/1982 | Riggs | 435/69.8 |
| 4,394,443 A | 7/1983 | Weissman et al. | 435/6 |
| 4,414,150 A | 11/1983 | Goeddel | 530/351 |
| 4,456,748 A | 6/1984 | Goeddel | 536/23.4 |
| 4,457,867 A | 7/1984 | Ishida | 530/324 |
| 4,518,584 A | 5/1985 | Mark et al. | 424/85.2 |
| 4,652,639 A | 3/1987 | Stabinsky | 536/23.1 |
| 4,663,290 A | 5/1987 | Weis et al. | 435/252.33 |
| 4,678,751 A | 7/1987 | Goeddel et al. | 435/252.3 |
| 4,695,623 A | 9/1987 | Stabinsky | 530/351 |
| 4,727,138 A | 2/1988 | Goeddel et al. | 536/23.52 |
| 4,762,791 A | 8/1988 | Goeddel et al. | 435/69.51 |
| 4,855,238 A | 8/1989 | Gray et al. | 439/69.51 |
| 4,925,793 A * | 5/1990 | Goeddel et al. | 435/69.51 |
| 4,929,554 A | 5/1990 | Goeddel et al. | 435/69.51 |

FOREIGN PATENT DOCUMENTS

| | | |
|---|---|---|
| EP | 0028033 | 5/1981 |
| EP | 0046039 A1 | 2/1982 |
| EP | 0063482 | 10/1982 |
| EP | 0077670 A3 | 4/1983 |
| EP | 0077670 A2 | 4/1983 |
| EP | 083777 A1 | 7/1983 |
| EP | 0095350 A2 | 11/1983 |
| EP | 0098118 A1 | 1/1984 |
| EP | 0121157 | 10/1984 |
| EP | 0128467 | 12/1984 |
| EP | 0136620 | 4/1985 |
| EP | 0146354 A2 | 6/1985 |
| EP | 0146413 A2 | 6/1985 |
| EP | 0146944 A2 | 7/1985 |
| EP | 0422697 A1 | 4/1991 |
| EP | 0423845 A1 | 4/1991 |
| EP | 0424990 A1 | 5/1991 |
| GB | 2040292 | 8/1980 |
| GB | 2063882 A | 6/1981 |
| GB | 2068970 A | 8/1981 |
| GB | 2071108 | 9/1981 |
| GB | 2079291 A | 1/1982 |
| GB | 2091268 | 7/1982 |
| WO | WO 81/03498 | 12/1981 |
| WO | WO 83/04053 | 11/1983 |
| WO | WO 85/04186 | 9/1985 |
| WO | WO 85/05619 | 12/1985 |
| WO | WO 86/06079 | 10/1986 |
| WO | WO 92/06707 | 4/1992 |
| WO | WO 93/21229 | 10/1993 |

OTHER PUBLICATIONS

Agarwal et al., "Total Synthesis of the Gene for an Alanine Transfer Ribonucleic Acid from Yeast," *Nature*, 227: 27–34 (1970).

Aharonowitz et al., "The Microbiological Production of Pharmaceuticals," *Sci. Amer.*, 245(3):140–152 (Sep., 1981).

Alton et al., "Production, Characterization and Biological Effects of Recombinant DNA Derived Human IFN–α and IFN–gamma Analogs," *The Biology of the Interferon System*, DeMaeyer et al. (eds.), Elsevier Science Pub. B. V., pp. 119–127 (1983) (*Proceedings 2nd Int. Meeting*).

Andrews et al., "Amino Acid Sequence of the Variable Regions of Heavy Chains from Two Idiotypically Cross–Reactive Human IgM Anti–Gamma–Globulins of the Wa Group," *Biochemistry*, 20:5828–5830 (1981).

Berger et al., "Characterization of Interferon Messenger RNA Synthesis in Namalva Cells," *J. Biol. Chem.*, 225(7):2955–2961 (1980).

"Biological Division Awards to Goeddel and Tijian," *Chem & Eng. News*, (Nov. 14, 1983).

Campbell et al.,"A microplaque reduction assay for human and mouse interferon[1]," *Can. J. Microbiol.*, 21:1247–1253 (1975).

Capon et al., "Bovine IFN Gene Families and Production of Ha–IFNs by Yeast and *E. coli*," The 3rd Annual International Congress for Interferon Research, (Abstract Only).

(Continued)

Primary Examiner—Janet Andres
(74) *Attorney, Agent, or Firm*—Marshall, Gerstein & Borun LLP

(57) ABSTRACT

Illustrated is the preparation and expression of manufactured genes capable of directing synthesis of human immune and leukocyte interferons and of other biologically active proteinaceous products, which products differ from naturally-occurring forms in terms of the identity and/or relative position of one or more amino acids, and in terms of one or more biological and pharmacological properties but which substantially retain other such properties.

3 Claims, 4 Drawing Sheets

OTHER PUBLICATIONS

Figure 1:
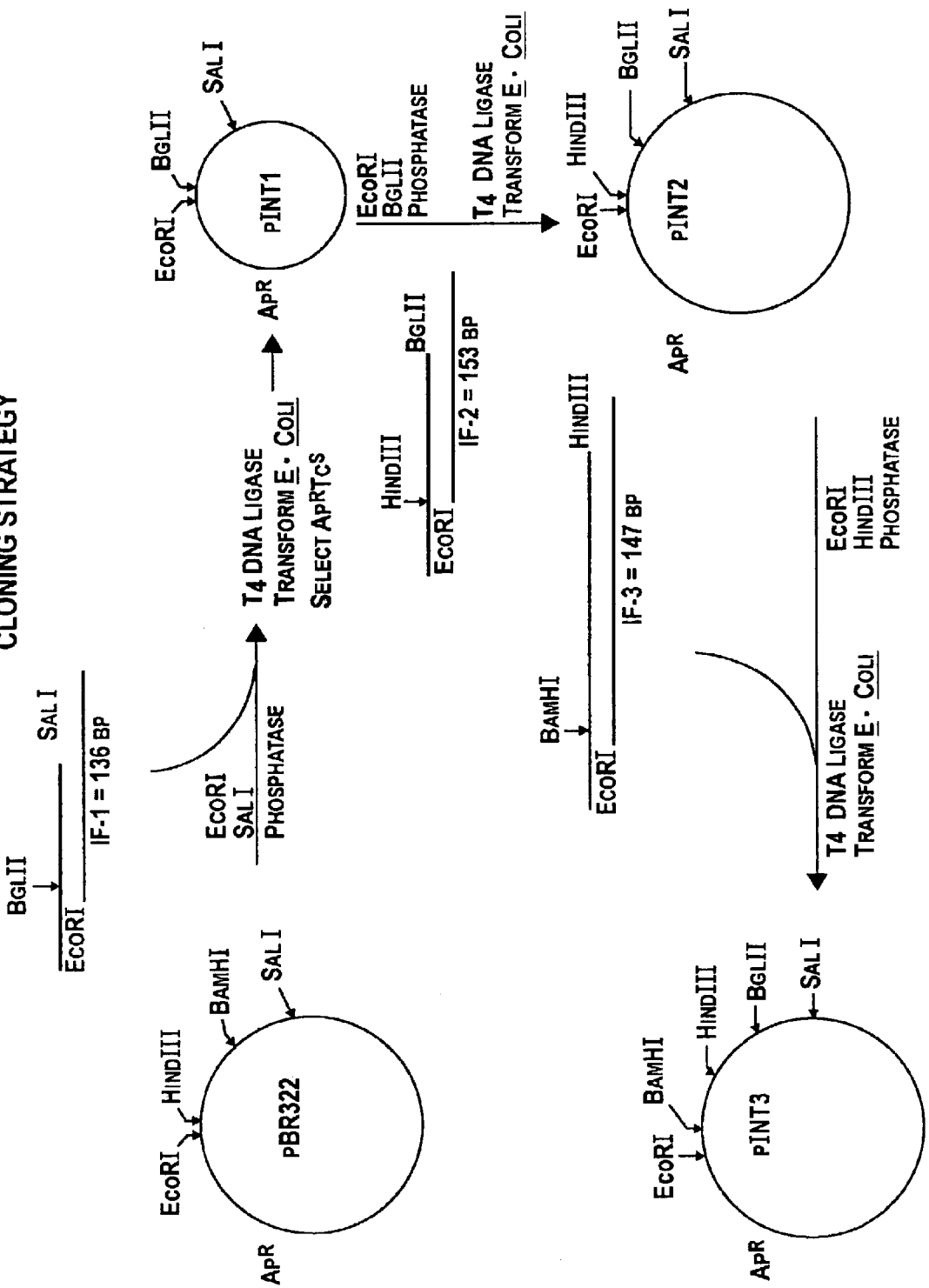

Dalboge et al., "In Vivo Processing of N–Terminal Methionine in *E. coli*," *FEBS*, 266(*1,2,1–3*):1–3 (Jun. 1990).

de Ley et al., "Interferon Induced in Human Leukocytes by Mitogens Production, Partial Purification and Characterization," *Eur. J. Immunol.*, 10:877–883 (1980).

Derynck et al., "Synthesis of Human Interferon–Gamma Derivatives in *E. coli*," Memo I A1193/2 (Aug., 1982).

Devos et al., "Molecular Cloning of Human Immune Interferon cDNA and its Expression in Eukaryotic Cells," *Nucl. Acids Res.*, 10(8):2487–2501 (Apr. 24, 1982).

Dianzani et al., "Immune and virus–induced interferons may activate cells by different derepressional mechanisms," *Nature*, 283:400 (1980).

Doolittle R.F., "Sequencing Peptides and Proteins Lacking Free α–Amino Groups," *Advanced Methods in Protein Sequence Determination*, Needleman (ed.), Springer–Verlag, Berlin, pp. 38–54 (1977).

Edge et al., "Total Synthesis of a Human Leukocyte Interferon Gene," *Nature*, 292(5825):756–762 (Aug. 20, 1981).

Epstein, "Interferon–Gamma: Is It Really Different From the Other Interferons?" in Interferon, Gresser (ed.), Academic Press, 3:13–44 (1981).

Epstein L.B., "Interferon as a Model Lymphokine," *Fed. Proc.*, 40(1):56–61 (1981).

Epstein, L.B., "Interferon–gamma: success, structure and speculation," *Nature*, 295:453–454 (1982).

Fiers et al., "Molecular–Biological Studies on Human Fibroblast Interferon, Immune Interferon and Interleukin 2 Genes," *The Biology of the Interferon System*, Elsevier Sci. Pub. B. V., DeMaeyer et al., (eds.), (1983).

Fiers et al., "The Human Fibroblast and Human Immune Interferon Genes and Their Expression in Homologous and Heterologous Cells", *Philos. Trans. R. Soc. Lond. B. Biol. Sci.*, 299(*1094*):29–38 (Sep. 24, 1982).

Fishbein, G.W., "Suntory Expresses Synthetic Gamma Interferon Gene," Newswatch, 2:5 (1982).

Gamma Winners, *Nature*, 294:7 (1981).

Gillis et al., "Biochemical Characterization of Lymphocyte Regulatory molecules: II. Purification of a Class of Rat and Human Lymphokines," *J. Immunol.*, 124(4):1954–1962 (Apr. 1980).

Goeddel et al., "Expression in *Escherichia coli* of chemically Synthesized Genes for Human Insulin," *Proc. Nat'l Acad. Sci., USA*, 76:106–110 (1979).

Goeddel et al., "Human Leukocyte Interferon Produced by *E. coli* is Biologically Active," *Nature*, 287:411–416 (1980).

Goeddel et al., "Synthesis of Human Fibroblasts Interferon by *E. coli*," *Nucl. Acids Res.*, 8(*18*):4057–4074 (Sep. 25, 1980).

Goeddel et al., "The Structure of Eight Distinct Cloned Human Leukocyte Interferon cDNAs," *Nature*, 290(*5801*):20–26 (Mar. 5, 1981).

Goeddel et al., Direct Expression in *Escherichia coli* of a DNA Sequence Coding for Human Growth Hormone,*Nature*, 281:544–548 (1981).

Gold et al., "Translational Initiation in Prokaryotes," *Ann. Rev. Microbiol.*, 35:365–403 (1981).

Grantham et al., "Codon Catalog Usage and the Genome Hypothesis," *Nucl. Acids Res.*, 8(*1*):r49–62 (1980).

Grantham et al., "Codon Catalog Usage is a Genome Strategy Modulated for Gene Expressivity," *Nucl. Acids Res.*, 9(*1*):r43–r74 (1981).

Grantham et al., "Codon Frequencies in 119 Individual Genes Confirm Consistent (Choices of Degenerate Bases According to Genome Type," *Nucl. Acids Res.*, 8(*9*):1893–1912 (1980).

Gray et al., "Expression of Human Immune Interferon cDNA in *E. coli* and Monkey Cells," *Nature*, 295:503–508 (Feb. 11, 1982).

Gray et al., "Structure of the Human Immune Interferon Gene," *Nature*, 298:859–863 (Aug. 26, 1982).

Hamer et al., "Expression of the chromosomal mouse β $^{maj}$–globin gene cloned in SV40," *Nature*, 281:35 (1979).

Hitzeman et al., "Expression of a Human Gene for Interferon in Yeast," *Nature*, 293:717721 (Oct. 29, 1981).

Horlein et al., Amino Acid Sequence of the Aminoterminal Segment of Dermatosparactic Calf–Skin Procollagen Type I, *Eur. J. Biochem*. 99:31–38 (1979).

Itakura et al., "Expression in *Escherichia coli* of a Chemically Synthesized Gene for the Hormone Somatostatin," *Science*, 198:1056–1063 (1977).

Khorana, "Total Synthesis of a Gene," *Science*, 203(*4381*):614–625 (Feb. 16, 1979).

Lewin, "Gene Expression," *Eucaryotic Chromosomes*, John Wiley & Sons, N.Y., 2:148–156 (1974).

Nathan et al., "Immune (Gamma) Interferon Produced by a Human T–Lymphoblast Cell Line," *Nature*, 292:842–844 (Aug. 27, 1981).

Novokhatskii et al., *Chem. Abstr.*, 96:120770 (1982).(first pub. in Dokl. Akad. Nauk SSSR, 261:997 (1981).

Pesicotta et al., "Purification and Characterization of the Amino–Terminal Peptide of Pro α1(I) Chains from Embryonic Chick Tendon Procollagen," *Amer. Chem. Soc.*, 19(*11*):2447–2453 (1980).

Podell et al., A Technique for the Removal of Pyroglutamic Acid from the Amino Terminus of Proteins Using Calf Liver Pyroglutamate Amino Peptidase, *Biochem. & Biophys. Res. Comm.*, 81(*1*):176–185 (Mar. 15, 1978).

Rigby P.W., "Expression of Cloned Genes in Eukaryotic Cells Using Vector Systems Derived from Replicons," pp. 83–141.

Rinderknecht et al., "Natural Human Interferon–Gamma: Complete Amino Acid Sequence and Determination of Sites of Glycosylation," *J. Biol. Chem.*, 259(*11*):6790–6797 (Jun. 10, 1984).

Roberts et al., *Proc. Nat'l Acad. Sci., USA*, 76:760 (1979).

Shepard et al., "A Single Amino Acid Change in IFN–$β_1$ Abolishes its Antiviral Activity," *Nature*, 294:563–565 (Dec. 10, 1981).

Sherman et al., "Methionine or Not Methionine at the Beginning of a Protein," *BioEssays*, 3(1):27–31.

Simonsen et al., "Plasmid–Directed Synthesis of Human Interferon in *E. coli* and Monkey Cells" *UCLA Symp. Mol. Cell. Biol., Interferons*, Academic Press, Inc., 25:1–14 (1982).

Stebbing et al., *Recombinant DNA Products, Insulin, Interferons and Growth Hormones*, A.P. Bollon, (ed.) CRC Press, (1983), pp. 75–114.

Stewart et al., (eds.), "Interferon Assays," *The Interferon System*, Springer–Verlag, N.Y., N.Y., Inc., pp. 13–26 (1979).

Tanaka et al., "Expression in *Escherichia coli* of Chemically Synthesized Gene for a Human Immune Interferon," *Nucl. Acids. Symp. Ser.*, (*11*):29–32 (Nov. 24, 1982).

Tanaka et al., "Expression in *E. coli* of Chemically Synthesized Genes for the Human Immune Interferon," *Nuc. Acids Res.*, 11(6):1707–1723 (1983).

Taniguchi et al., "Partial characterization of γ (immune) interfereon mRNA extracted from human lymphocytes," *Proc. Nat'l Acad. Sci.*, 78:3469–3472 (1981).

"The Big IF in Cancer," *Time*, 60–66 (Mar. 31, 1980).

Ullrich et al., "Rat Insulin Genes: Construction of Plasmids Containing the Coding Sequences," *Science*, 196(4296):1313–1319 (Jun. 17, 1977).

Vilcek et al., "The Importance of Having Gamma," *Interferon*, 4:129–154 (1982).

Vilcek et al., "Synthesis and Properties of Various Human Interferons," *Microbiol.*, 204–207 (1980).

Wallace et al.,"Translation of Human Immune Interferon Messenger RNA in Xenopus Laevis Oocytes," *Biochem. Biophys. Res. Commun.*, 100:865 (1981).

Wallace et al.,"Production of Immune Interferon and its mRNA by Activated Cultured Human Leukocytes," *Fed. Proc.*, 40:1574 (1981).

Watson, *Molecular Biology of the Gene*, Third Edition,W .A. Benjamin, Inc., Menlo Park, Cal., p. 225, (1976).

Weck et al., "Antiviral Activities of Hybrids of Two Major Human Leukocyte Interferons," *Nucl. Acids Res.*, 9(22):6153–6166 (Nov. 25, 1981).

Weening et al., "Messenger RNA of Human Immune Interferon: Isolation and Partial Characterization," *Biochem. Biophys. Res. Comm.*, 104(1):6–13 (Jan. 15, 1982).

Weissenbach et al., "Two interferon mRNAs in human fibroblasts: In vitro translation and *Escherichio coli* cloning studies," *Proc. Nat'l. Acad. Sci (USA)* 77:7152–56 (1980).

Weissenbach et al., "Identification of the Translation Products in Human Fibroblast Interferon mRNA in Reticulocyte Lysates," *Eur. J. Biochem.* 98:1–8 (1979).

Weissman, "The Cloning of Interferon and Other Mistakes," in Interferon, Gresser (ed.), *Academic Press,* 3:101–134 (1981).

Weissman, "Future Trends: Reversed Genetics," *Trends in Biochemical Science*, pp. N109–111 (May 1978).

Weissman et al., "Structure and Expression of Human Alpha–Interferon Genes," *UCLA Symp. Mol. Cell. Biol.,* 25:295–326 (1982).

Yip et al., "Molecular Weight of Human Gamma Interferon Is Similar to That of Other Human Interferons," *Science,* 215:411–413 (1982).

Yip et al., "Partial Purification and Characterization of Human (Immune) Interferon," *Proc. Nat'l Acad. Sci., USA*, 78:1601–1605 (1981).

* cited by examiner

FIG. 2A

```
                                      1          2           3           4           5          6
                                      0          0           0           0           0          0
   ┌ IFN-αJ/(2)        CDLPQTHSLGSRRTLMLL AQMRKIS LFSCLKDRHDFGFPQEEF- GNQFQKAETI PVLHEM
   │ IFN-αD/(1)        CDLPETHSLDNRRTLMLL AQMSRIS PSSCLMDRHDFGFPQEEFDGNQFQKAPAI SVLHEL
 I │ IFN-α5/(G)        CDLPQTHSLSNRRTLMI  AQMSRIS PFSCLKDRHDFGFPQEEFDGNQFQKAPAI SVLHEM
   │ IFN-α6/K          CDLPQTHSLCHRRTMMLL MAQMGRIS PFSCLKDRHDFRFPQEEFDGNQFQKAEAI SVLHEV
   └ IFN-αC            CDLPQTHSLCHRRTMMLL AQMRRIS LFSCLKDRHDFGFPQEEFPQ  GNQFQKAEAI SVLHEM
   ┌ IFN-αC₁           CDLPQTHSLRNRRALILL GQMGRIS PFSCLKDRHDFRI PQEEFDGNQFQKAQAI SVLHEM
   │ IFN-α4b/(4a)      CDLPQTHSLGNRRALILL AQMGRIS PFSCLKDRPDFGLPQEEFDGNQFQKTQAI SVLHEM
 II│ IFN-αI            CDLPQTHSLRNRRALILL AQMGRIS HFSCLKDRHDFGFPE EEFDGHQFQKTQAI SVLHEM
   │ IFN-αL            CDLPQTHSLRNRRALILL AQMGRIS PFSCLKDRPDFGLPQEEFDGNQFQKAQAI SVLHEM
   └ IFN-αJ/7          CDLPQTHTLRNRRALILL AQMGRIS PFSCLKDRHDFRI PQEEFDGHQFQKAQAI SVLHEM
     IFN-αH/(2λH)/(H₁) CDLPQTHSLNNRRALILL GQMGRIS PFSCLKDRHEFRFPE EEFDGHQFQKTQAI SVLHEM
     IFN-αF            CNLSQTHSLGNRRTLML  MAQMRRIS PFSCLKDRHDFEFPQGFPQEEFDGNQFQKAQAI SVLHEM
     IFN-αB/8/(B2)     CDLPQTHSLGNRRALILL AQMRRIS PFSCLKDRHDFGFPQ EEFDD KQFQKAQAI SVLHEM
                                  G
     IFN-αCon1         CDLPQTHSL    RRALILL AQMRRIS PFSCLKDRHDFGFPQEEFDGNQFQKAQAI SVLHEM
```

FIG. 2B

```
                                    70              80              90             100             110         120
                                                                                                                 2
                                                                                                                 0
I  ┌ IFN-αA/(2)          IQQIFNLFSTKDSSAAWDETLLDKFYTELYQQLNDLEACVIQGVGVTETPLMKEDSILAV
   │ IFN-αD/(1)          IQQIFNLFTTKDSSAAWDEDLLDKFYTELYQQLNDEEACVMQEERVGETPLMNVDSILAV
   │ IFN-α5/(G)          IQQTFNLFSTKDSSATWDETLLDKFYTELYQQLNDLEACMMQEVGVEDTPLMNVDSILTV
   └ IFN-α6/K            IQQTFNLFSTKDSSVAWDERLLDKLYTELYQQLNDLEACVMQEVWVGGTPLMNEDSILAV
     IFN-αC              IQQTFNLFSTEDSSAAWEQSLLEKFSTELYQQLNDLEACVIQEVGVEETPLMNEDSILAV
II ┌ IFN-αC1             IQQTFNLFSTEDSSAAWEQSLLEKFSTELYQQLNDLEACVIQEVGMEQTPLMNEDSILAV
   │ IFN-α4b/(4a)        IQQTFNLFSTEDSSAAWEQSLLEKFSTELYQQLNDLEACVIQEVGVEETPLMNVDSILAV
   │ IFN-αI              IQQTFNLFSTEDSSAAWEQSLLEKFSTELYQQLNDLEACVIQEVGMEETPLMNEDSILAV
   │ IFN-αL              IQQTFNLFSTEDSSAAWEQSLLELFSTELYQQLNDLEACVIQEVGVEETPLMNEDSILAV
   └ IFN-αJ7             IQQTFNLFSTEDSSAAWEQSLLEKFSTELYQQLNDLEACVIQEVGVKETPLMNEDFILAV
     IFN-αH/(2λH)/(H1)   MQQTFNLFSTKNSSAAWDETLLEKFYIELFQQMNDLEACVIQEVGVEETPLMNEDSILAV
     IFN-αF              IQQTFNLFSTKDSSATWEQSLLEKFSTELNQQLNDMEACVIQEVGVEETPLMNVDSILAV
     IFN-αB/8/(B2)       IQQTFNLFSTKDSSAALDETLLDEFYIELDQQLNDLEVLCDQEVGVIESPLMYEDSILAV

IFN-αCon1           IQQTFNLFSTKDSSAAWDESLLEKFYTELYQQLNDLEACVIQEVGVEETPLMNVDSILAV
```

FIG. 2C

| | | 10 | 40 | 50 | 60 | Number Unique |
|---|---|---|---|---|---|---|
| I { | IFN-αA/(2) | RKYFQRITLYLK | EKKYS PCA WEVVRAEIMRSFSLS | TNLQESLRSKE | | 7 (7) |
| | IFN-αD/(1) | KKYFQRITLYLT | EKKYS PCA WEVVRAEIMRSLSLS | TNLQERLRRKE | | 13 (14) |
| | IFN-α5/(G) | RKYFQRITLYLT | EKKYS PCA WEVVRAEIMRSFSLS | ANLQERLRRKE | | 5 (4) |
| | IFN-α6/K | RKYFQRITLYLT | EKKYS PCA WEVVRAEIMRSFSSS | RNLQERLRRKE | | 10 |
| II { | IFN-αC | RKYFQRITLYLI | ERKYS PCA WEVVRAEIMRSLSFS | TNLQKRLRRKD | | 0 |
| | IFN-αC1 | RKYFQRITLYLT | EKKYS PCA WEVVRAEIMRSLSFS | TNLQKRLRRKD | | 1 |
| | IFN-α4b/(4a) | RKYFQRITLYLT | EKKYS PCA WEVVRAEIMRSLSFS | TNLQKRLRRKD | | 1 (1) |
| | IFN-αI | RKYFQRITLYLI | ERKYS PCA WEVVRAEIMRSLSFS | TNLQKI LRRKD | | 0 |
| | IFN-αL | RKYFQRITLYLM | EKKYS PCA WEVVRAEIMRSFSFS | TNLKKGLRRKD | | 2 |
| | IFN-αJ7 | RKYFQRITLYLM | EKKYS PCA WEVVRAEIMRSFSFS | TNLQKRLRRKD | | 5 |
| | IFN-αH/(2λH)/(H1) | RKYFQRITLYLT | EKKYS PCA WEVVRAEIMRSFSLS | KI FQERLRRKE | | 5 (5) |
| | IFN-αF | KKYFQRITLYLT | EKKYS PCA WEVVRAEIMRSFSLS | KI NLQKRLKSKE | | 5 |
| | IFN-αB/8/(B2) | RKYFQRITLYLT | EKKYS SCA WEVVRAEIMRSFSLS | I NLQKRLKSKE | | 15 (12) |
| | IFN-αCon1 | KKYFQRITLYLT | EKKYS PCA WEVVRAEIMRSFSLS | TNLQERLRRKE | | |

MANUFACTURE AND EXPRESSION OF LARGE STRUCTURAL GENES

This is a Continuation of U.S. application Ser. No. 06/483,451, filed Apr. 15, 1983, which is a continuation-in-part of Ser. No. 06/375,494 filed May 6, 1982, abandoned.

The present invention relates generally to the manipulation of genetic materials and, more particularly, to the manufacture of specific DNA sequences useful in recombinant procedures to secure the production of proteins of interest.

Genetic materials may be broadly defined as those chemical substances which program for and guide the manufacture of constituents of cells and viruses and direct the responses of cells and viruses. A long chain polymeric substance known as deoxyribonucleic acid (DNA) comprises the genetic material of all living cells and viruses except for certain viruses which are programmed by ribonucleic acids (RNA). The repeating units in DNA polymers are four different nucleotides, each of which consists of either a purine (adenine or guanine) or a pyrimidine (thymine or cytosine) bound to a deoxyribose sugar to which a phosphate group is attached. Attachment of nucleotides in linear polymeric form is by means of fusion of the 5' phosphate of one nucleotide to the 3' hydroxyl group of another. Functional DNA occurs in the form of stable double stranded associations of single strands of nucleotides (known as deoxyoligonucleotides), which associations occur by means of hydrogen bonding between purine and pyrimidine bases [i.e., "complementary" associations existing either between adenine (A) and thymine (T) or guanine (G) and cytosine (C)]. By convention, nucleotides are referred to by the names of their constituent purine or pyrimidine bases, and the complementary associations of nucleotides in double stranded DNA (i.e., A-T and G-C) are referred to as "base pairs". Ribonucleic acid is a polynucleotide comprising adenine, guanine, cytosine and uracil (U), rather than thymine, bound to ribose and a phosphate group.

Most briefly put, the programming function of DNA is generally effected through a process wherein specific DNA nucleotide sequences (genes) are "transcribed" into relatively unstable messenger RNA (mRNA) polymers. The mRNA, in turn, serves as a template for the formation of structural, regulatory and catalytic proteins from amino acids. This translation process involves the operations of small RNA strands (tRNA) which transport and align individual amino acids along the mRNA strand to allow for formation of polypeptides in proper amino acid sequences. The mRNA "message", derived from DNA and providing the basis for the tRNA supply and orientation of any given one of the twenty amino acids for polypeptide "expression", is in the form of triplet "codons"—sequential groupings of three nucleotide bases. In one sense, the formation of a protein is the ultimate form of "expression" of the programmed genetic message provided by the nucleotide sequence of a gene.

Certain DNA sequences which usually "precede" a gene in a DNA polymer provide a site for initiation of the transcription into mRNA. These are referred to as "promoter" sequences. Other DNA sequences, also usually "upstream" of (i.e., preceding) a gene in a given DNA polymer, bind proteins that determine the frequency (or rate) of transcription initiation. These other sequences are referred to as "regulator" sequences. Thus, sequences which precede a selected gene (or series of genes) in a functional DNA polymer and which operate to determine whether the transcription (and eventual expression) of a gene will take place are collectively referred to as "promoter/regulator" or "control" DNA sequences. DNA sequences which "follow" a gene in a DNA polymer and provide a signal for termination of the transcription into mRNA are referred to as "terminator" sequences.

A focus of microbiological processing for nearly the last decade has been the attempt to manufacture industrially and pharmaceutically significant substances using organisms which do not initially have genetically coded information concerning the desired product included in their DNA. Simply put, a gene that specifies the structure of a product is either isolated from a "donor" organism or chemically synthesized and then stably introduced into another organism which is preferably a self-replicating unicellular microorganism. Once this is done, the existing machinery for gene expression in the "transformed" host cells operates to construct the desired product.

The art is rich in patent and literature publications relating to "recombinant DNA" methodologies for the isolation, synthesis, purification and amplification of genetic materials for use in the transformation of selected host organisms. U.S. Pat. No. 4,237,224 to Cohen, et al., for example, relates to transformation of procaryotic unicellular host organisms with "hybrid" viral or circular plasmid DNA which includes selected exogenous DNA sequences. The procedures of the Cohen, et al. patent first involve manufacture of a transformation vector by enzymatically cleaving viral or circular plasmid DNA to form linear DNA strands. Selected foreign DNA strands are also prepared in linear form through use of similar enzymes. The linear viral or plasmid DNA is incubated with the foreign DNA in the presence of ligating enzymes capable of effecting a restoration process and "hybrid" vectors are formed which include the selected foreign DNA segment "spliced" into the viral or circular DNA plasmid.

Transformation of compatible unicellular host organisms with the hybrid vector results in the formation of multiple copies of the foreign DNA in the host cell population. In some instances, the desired result is simply the amplification of the foreign DNA and the "product" harvested is DNA. More frequently, the goal of transformation is the expression by the host cells of the foreign DNA in the form of large scale synthesis of isolatable quantities of commercially significant protein or polypeptide fragments coded for by the foreign DNA. See also, e.g., U.S. Pat. No. 4,269,731 (to Shine), U.S. Pat. No. 4,273,875 (to manis) and U.S. Pat. No. 4,293,652 (to Cohen).

The success of procedures such as described in the Cohen, et al. patent is due in large part to enyzmes which facilitate the site-specific cleavage of both the unhybridized DNA vector and, e.g., eukaryotic DNA strands containing the foreign sequences of interest. Cleavage in a manner providing for the formation of single stranded complementary "ends" on the double stranded linear DNA strands greatly enhances the likelihood of functional incorporation of the foreign DNA into the vector upon "ligating" enzyme treatment. A large number of such restriction endonuclease enzymes are currently commercially available [See, e.g., "BRL Restriction Endonuclease Reference Chart" appearing in the "'81/'82 Catalog" of Bethesda Research Laboratories, Inc., Gaithersburg, Md.] Verification of hybrid formation is facilitated by chromatographic techniques which can, for example, distinguish the hybrid plasmids from non-hybrids on the basis of molecular weight. Other useful verification techniques involve radioactive DNA hybridization.

Another manipulative "tool" largely responsible for successes in transformation of procaryotic cells is the use of selectable "marker" gene sequences. Briefly put, hybrid vectors are employed which contain, in addition to the desired foreign DNA, one or more DNA sequences which code for expression of a phenotypic trait capable of distinguishing transformed from non-transformed host cells. Typical marker gene sequences are those which allow a transformed procaryotic cell to survive and propagate in a culture medium containing metals, antibiotics, and like components which would kill or severely inhibit propagation of non-transformed host cells.

Successful expression of an exogenous gene in a transformed host microorganism depends to a great extent on incorporation of the gene into a transformation vector with a suitable promoter/regulator region present to insure transcription of the gene into mRNA and other signals which insure translation of the mRNA message into protein (e.g., ribosome binding sites). It is not often the case that the "original" promoter/regulator region of a gene will allow for high levels of expression in the new host. Consequently, the gene to be inserted must either be fitted with a new, host-accommodated transcription and translation regulating DNA sequence prior to insertion or it must be inserted at a site where it will come under the control of existing transcription and translation signals in the vector DNA.

It is frequently the case that the insertion of an exogenous gene into, e.g., a circular DNA plasmid vector, is performed at a site either immediately following an extant transcription and translation signal or within an existing plasmid-borne gene coding for a rather large protein which is the subject of high degrees of expression in the host. In the latter case, the host's expression of the "fusion gene" so formed results in high levels of production of a "fusion protein" including the desired protein sequence (e.g., as an intermediate segment which can be isolated by chemical cleavage of large protein). Such procedures not only insure desired regulation and high levels of expression of the exogenous gene product but also result in a degree of protection of the desired protein product from attack by proteases endogenous to the host. Further, depending on the host organism, such procedures may allow for a kind of "piggyback" transportation of the desired protein from the host cells into the cell culture medium, eliminating the need to destroy host cells for the purpose of isolating the desired product.

While the foregoing generalized descriptions of published recombinant DNA methodologies may make the processes appear to be rather straightforward, easily performed and readily verified, it is actually the case that the DNA sequence manipulations involved are quite painstakingly difficult to perform and almost invariably characterized by very low yields of desired products.

As an example, the initial "preparation" of a gene for insertion into a vector to be used in transformation of a host microorganism can be an enormously difficult process, especially where the gene to be expressed is endogenous to a higher organism such as man. One laborious procedure practiced in the art is the systematic cloning into recombinant plasmids of the total DNA genome of the "donor" cells, generating immense "libraries" of transformed cells carrying random DNA sequence fragments which must be individually tested for expression of a product of interest. According to another procedure, total mRNA is isolated from high expression donor cells (presumptively containing multiple copies of mRNA coded for the product of interest), first copied, into single stranded cDNA with reverse transcriptase enzymes, then into double stranded form with polymerase, and cloned. The procedure again generates a library of transformed cells somewhat smaller than a total genome library which may include the desired gene copies free of non-transcribed "introns" which can significantly interfere with expression by a host microorganism. The above-noted time-consuming gene isolation procedures were in fact employed in published recombinant DNA procedures for obtaining microorganism expression of several proteins, including rat proinsulin [Ullrich, et al., *Science*, 196, pp. 1313–1318 (1977)], human fibroblast interferon [Goedell, et al., *Nucleic Acids Research*, 8, pp. 4087–4094 (1980)], mouse β-endorphin [Shine, et al., *Nature*, 285, pp. 456–461 (1980)] and human leukocyte interferon (Goedell, et al., *Nature*, 287, pp. 411–416 (1980); and Goedell, et al., *Nature*, 290, pp. 20–26 (1981)).

Whenever possible, the partial or total manufacture of genes of interest from nucleotide bases constitutes a much preferred procedure for preparation of genes to be used in recombinant DNA methods. A requirement for such manufacture is, of course, knowledge of the correct amino acid sequence of the desired polypeptide. With this information in hand, a generative DNA sequence code for the protein (i.e., a properly ordered series of base triplet codons) can be planned and a corresponding synthetic, double stranded DNA segment can be constructed. A combination of manufacturing and cDNA synthetic methodologies is reported to have been employed in the generation of a gene for human growth hormone. Specifically, a manufactured linear double stranded DNA sequence of 72 nucleotide base pairs (comprising codons specifying the first 24 amino acids of the desired 191 amino acid polypeptide) was ligated to a cDNA-derived double strand coding for amino acids Nos. 25–191 and inserted in a modified pBR322 plasmid at a locus controlled by a lac promotor/regulator sequence [Goedell, et al., *Nature*, 281, pp. 544–548 (1981)).

Completely synthetic procedures have been employed for the manufacture of genes coding for relatively "short" biologically functional polypeptides, such as human somatostatin (14 amino acids) and human insulin (2 polypeptide chains of 21 and 30 amino acids, respectively).

In the somatostatin gene preparative procedure [Itakura, et al., *Science*, 198, pp. 1056–1063 (1977)) a 52 base pair gene was constructed wherein 42 base pairs represented the codons specifying the required 14 amino acids and an additional 10 base pairs were added to permit formation of "sticky-end" single stranded terminal regions employed for ligating the structural gene into a microorganism transformation vector. Specifically, the gene was inserted close to the end of a β-galactosidase enzyme gene and the resultant fusion gene was expressed as a fusion protein from which somatostatin was isolated by cyanogen bromide cleavage. Manufacture of the human insulin gene, as noted above, involved preparation of genes coding for a 21 amino acid chain and for a 30 amino acid chain. Eighteen deoxyoligonucleotide fragments were combined to make the gene for the longer chain, and eleven fragments were joined into a gene for the shorter chain. Each gene was employed to form a fusion gene with a β-galactosidase gene and the individually expressed polypeptide chains were enzymatically isolated and linked to form complete insulin molecules. [Goedell, et al., *Proc. Nat. Acad. Sci. U.S.A.*, 76, pp. 106–110 (1979).]

In each of the above procedures, deoxyoligonucleotide segments were prepared, and then sequentially ligated according to the following general procedure. [See, e.g., Agarwal, et al., *Nature*, 227, pp. 1–7 (1970) and Khorana, *Science*, 203, pp. 614–675 (1979)]. An initial "top" (i.e., 5'-3' polarity) deoxyoligonucleotide segment is enzymatically joined to a second "top" segment. Alignment of these two "top" strands is made possible using a "bottom" (i.e., 3' to 5' polarity) strand having a base sequence complementary to half of the first top strand and half of the second top strand. After joining, the uncomplemented bases of the top strands "protrude" from the duplex portion formed. A second bottom strand is added which includes the five or six base complement of a protruding top strand, plus an additional five or six bases which then protrude as a bottom single stranded portion. The two bottom strands are then joined. Such sequential additions are continued until a complete gene sequence is developed, with the total procedure being very time-consuming and highly inefficient.

The time-consuming characteristics of such methods for total gene synthesis are exemplified by reports that three months' work by at least four investigators was needed to perform the assembly of the two "short", insulin genes previously referred to. Further, while only relatively small quantities of any manufactured gene are needed for success of vector insertion, the above synthetic procedures have such poor overall yields (on the order of 20% per ligation) that the eventual isolation of even minute quantities of a selected short gene is by no means guaranteed with even the most scrupulous adherence to prescribed methods. The maximum length gene which can be synthesized is clearly limited by the efficiency with which the individual short segments can be joined. If n such ligation reactions are required and the yield of each such reaction is y, the quantity of correctly synthesized genetic material obtained will be proportional to $y^n$. Since this relationship is expotential in nature, even a small increase in the yield per ligation reaction will result in a substantial increase in the length of the largest gene that may be synthesized.

Inefficiencies in the above-noted methodology are due in large part to the formation of undesired intermediate products. As an example, in an initial reaction forming annealed top strands associated with a bottom, "template" strand, the desired reaction may be,

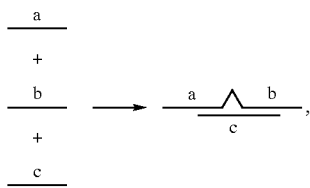

but the actual products obtained may be

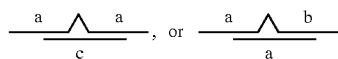

or the like. Further, the longer the individual deoxyolidonucleotides are, the more likely it is that they will form thermodynamically stable self-associations such as "hairpins" or aggregations.

Proposals for increasing synthetic efficiency have not been forthcoming and it was recently reported that, "With the methods now available, however, it is not economically practical to synthesize genes for peptides longer than about 30 amino acid units, and many clinically important proteins are much longer". [Aharonowitz, et al. *Scientific American*, 245, No. 3, pp. 140–152, at p. 151 (1981).]

An illustration of the "economic practicalities" involved in large gene synthesis is provided by the recent publication of "successful" efforts in the total synthesis of a human leukocyte interferon gene. [Edge, et al. *Nature*, 292, pp. 756–782 (1981).] Briefly summarized, 67 different deoxyoligonucleotides containing about 15 bases were synthesized and joined in the "50 percent overlap" procedure of the type noted above to form eleven short duplexes. These, in turn were assembled into four longer duplexes which were eventually joined to provide a 514 base pair gene coding for the 166 amino acid protein. The procedure, which the authors characterize as "rapid", is reliably estimated to have consumed nearly a year's effort by five workers and the efficiency of the assembly strategy was clearly quite poor. It may be noted, for example, that while 40 pmole of each of the starting 67 deoxyoligonucleotides was prepared and employed to form the eleven intermediate-sized duplexes, by the time assembly of the four large duplexes was achieved, a yield of only about 0.01 pmole of the longer duplexes could be obtained for use in final assembly of the whole gene.

Another aspect of the practice of recombinant DNA techniques for the expression, by microorganisms, of proteins of industrial and pharmaceutical interest is the phenomenon of "codon preference". While it was earlier noted that the existing machinery for gene expression in genetically transformed host cells will "operate" to construct a given desired product, levels of expression attained in a microorganism can be subject to wide variation, depending in part on specific alternative forms of the amino acid-specifying genetic code present in an inserted exogenous gene. A "triplet" codon of four possible nucleotide bases can exist in 64 variant forms. That these forms provide the message for only 20 different amino acids (as well as transcription initiation and termination) means that some amino acids can be coded for by more than one codon. Indeed, some amino acids have as many as six "redundant", alternative codons while some others have a single, required codon. For reasons not completely understood, alternative codons are not at all uniformly present in the endogenous DNA of differing types of cells and there appears to exist a variable natural hierarchy or "preference" for certain codons in certain types of cells.

As one example, the amino acid leucine is specified by any of six DNA codons including CTA, CTC, CTG, CTT, TTA, and TTG (which correspond, respectively, to the mRNA codons, CUA, CUC, CUG, CUU, UUA and UUG). Exhaustive analysis of genome codon frequencies for microorganisms has revealed endogenous DNA of *E. coli* bacteria most commonly contains the CTG leucine-specifying codon, while the DNA of yeasts and slime molds most commonly includes a TTA leucine-specifying codon. In view of this hierarchy, it is generally held that the likelihood of obtaining high levels of expression of a leucine-rich polypeptide by an *E. coli* host will depend to some extent on the frequency of codon use. For example, a gene rich in TTA codons will in all probability be poorly expressed in *E. coli*, whereas a CTG rich gene will probably highly express the polypeptide. In a like manner, when yeast cells are the projected transformation host cells for expression of a leucine-rich polypeptide, a preferred codon for use in an inserted DNA would be TTA. See, e.g., Grantham, et al. *Nucleic Acids Research*, 8, pp. r49–r62 (1980); Grantham, et al., *Nucleic Acids Research*, 8, pp. 1893–1912 (1980); and, Grantham, et al., *Nucleic Acids Research*, 9, pp. r43–r74 (1981).

The implications of codon preference phenomena on recombinant DNA techniques are manifest, and the phenomenon may serve to explain many prior failures to achieve high expression levels for exogenous genes in successfully transformed host organisms—a less "preferred" codon may be repeatedly present in the inserted gene and the host cell machinery for expression may not operate as efficiently. This phenomenon directs the conclusion that wholly manufactured genes which have been designed to include a projected host cell's preferred codons provide a preferred form of foreign genetic material for practice of recombinant DNA techniques. In this context, the absence of procedures for rapid and efficient total gene manufacture which would permit codon selection is seen to constitute an even more serious roadblock to advances in the art.

Of substantial interest to the background of the present invention is the state of the art with regard to the preparation and use of a class of biologically active substances, the interferons (IFNs). Interferons are secreted proteins having fairly well-defined antiviral, antitumor and immunomodulatory characteristics. See, e.g., Gray, et al., *Nature*, 295, pp. 503–508 (1982) and Edge, et al., supra, and references cites therein.

On the basis of antigenicity and biological and chemical properties, human interferons have been grouped into three major classes: IFN-α (leukocyte), IFN-β (fibroblast) and IFN-γ (immune). Considerable information has accumulated on the structures and properties of the virus-induced acid-stable interferons (IFN-α and β). These have been purified to homogeneity and at least partial amino acid sequences have been determined. Analyses of cloned cDNA and gene sequences for IFN-β$_1$ and the IFN-α multigene family have permitted the deduction of the complete amino acid sequences of many of the interferons. In addition, efficient synthesis of IFN-β$_1$ and several IFN-αs in *E. coli*, and IFN-α$_1$, in yeast, have now made possible the purification of large quantities of these proteins in biologically active form.

Much less information is available concerning the structure and properties of IFN-γ, an interferon generally produced in cultures of lymphocytes exposed to various mitogenic stimuli. It is acid labile and does not cross-react with antisera prepared against IFN-α or IFN-β. A broad range of biological activities have been attributed to IFN-γ including potentiation of the antiviral activities of IFN-α and -β, from which it differs in terms of its virus and cell specificities and the antiviral mechanisms induced. In vitro studies performed with crude preparations suggest that the primary function of IFN-γ may be as an immunoregulatory agent. The antiproliferative effect of IFN-γ on transformed cells has been reported to be 10 to 100-fold greater than that of IFN-α or -β, suggesting a potential use in the treatment of neoplasia. Murine IFN-γ preparations have been shown to have significant antitumor activity against mouse sarcomas.

It has recently been reported (Gray, et al., supra) that a recombinant plasmid containing a cDNA sequence coding for human IFN-γ has been isolated and characterized. Expression of this sequence in *E. coli* and cultured monkey cells is reported to give rise to a polypeptide having the properties of authentic human IFN-γ. In the publication, the cDNA sequence and the deduced 146 amino acid sequence of the "mature" polypeptide, exclusive of the putative leader sequence, is as follows:

```
1                                         10
Cys-Tyr-Cys-Gln-Asp-Pro-Tyr-Val-Lys-Glu-Ala-Glu-
TGT TAC TGC CAG CAG CAA TAT GTA AAA GAA GCA GAA

20
Asn-Leu-Lys-Lys-Tyr-Phe-Asn-Ala-Gly-His-Ser-Asp-
AAC CTT AAG AAA TAT TTT AAT GCA GGT CAT TCA GAT
```

-continued
```
                    30
Val-Ala-Asp-Asn-Gly-Thr-Leu-Phe-Leu-Gly-Ile-Leu-
GTA GCG GAT AAT GGA ACT CTT TTC TTA GGC ATT TTG 40
Lys-Asn-Trp-Lys-Glu-Glu-Ser-Asp-Arg-Lys-Ile-Met-
AAG AAT TGG AAA GAG GAG AGT GAC AGA AAA ATA ATG 50                                    60
Gln-Ser-Gln-Ile-Val-Ser-Phe-Tyr-Phe-Lys-Leu-Phe-
CAG AGC CAA ATT GTC TCC TTT TAC TTC AAA CTT TTT 70
Lys-Asn-Phe-Lys-Asp-Asp-Gln-Ser-Ile-Gln-Lys-Ser-
AAA AAC TTT AAA GAT GAC CAG AGC ATC CAA AAG AGT 80
Val-Glu-Thr-Ile-Lys-Glu-Asp-Met-Asn-Val-Lys-Phe-
GTG GAG ACC ATC AAG GAA GAC ATG AAT GTC AAG TTT 90
Phe-Asn-Ser-Asn-Lys-Lys-Lys-Arg-Asp-Asp-Phe-Glu-
TTC AAT AGC AAC AAA AAG AAA CGA GAT GAC TTC GAA 100
Lys-Leu-Thr-Asn-Tyr-Ser-Val-Thr-Asp-Leu-Asn-Val-
AAG CTG ACT AAT TAT TCG GTA ACT GAC TTG AAT GTC 110                                   120
Gln-Arg-Lys-Ala-Ile-His-Glu-Leu-Ile-Gln-Val-Met-
CAA CGC AAA GCA ATA CAT GAA CTC CTC ATC CAA ATG 130
Ala-Glu-Leu-Ser-Pro-Ala-Ala-Lys-Thr-Gly-Lys-Arg-
GCT GAA CTG TCG CAA GCA GCT AAA ACA GGG AAG CGA 140
Lys-Arg-Ser-Gln-Met-Leu-Phe-Gln-Gly-Arg-Arg-Ala-
AAA AGG AGT CAG ATG CTG TTT CAA GGT CGA AGA GCA 146
Ser-Gln
TCC CAG.
```

In a previous publication of the sequence, arginine, rather than glutamine, was specified at position 140 in the sequence. (Unless otherwise indicated, therefore, reference to "human immune interferon" or, simply "IFN-γ" shall comprehend both the [Arg$^{140}$] and [Gln$^{140}$] forms.)

The above-noted wide variations in biological activities of various interferon types makes the construction of synthetic polypeptide analogs of the interferons of paramount significance to the full development of the therapeutic potential of this class of compounds. Despite the advantages in isolation of quantities of interferons which have been provided by recombinant DNA techniques to date, practitioners in this field have not been able to address the matter of preparation of synthetic polypeptide analogs of the interferons with any significant degree of success.

Put another way, the work of Gray, et al., supra, in the isolation of a gene coding for IFN-γ and the extensive labors of Edge, et al., supra, in providing a wholly manufactured IFN-α$_1$ gene provide only genetic materials for expression of single, very precisely defined, polypeptide sequences. There exist no procedures (except, possibly, for site specific mutagenesis) which would permit microbial expression of large quantities of human IFN-γ analogs which differed from the "authentic" polypeptide in terms of the identity or location of even a single amino acid. In a like manner, preparation of an IFN-α$_1$ analog which differed by one amino acid from the polypeptide prepared by Edge, et al., supra, would appear to require an additional year of labor in constructing a whole new gene which varied in terms of a single triplet codon. No means is readily available for the excision of a fragment of the subject gene and replacement with a fragment including the coding information for a variant polypeptide sequence. Further, modification of the reported cDNA-derived and manufactured DNA sequences to vary codon usage is not an available "option".

Indeed, the only report of the preparation of variant interferon polypeptide species by recombinant DNA techniques has been in the context of preparation and expression of "hybrids" of human genes for IFN-$\alpha_1$ and IFN-$\alpha_2$ [Weck, et al., *Nucleic Acids Research*, 9, pp. 6153–6168 (1981) and Streuli, et al., *Proc. Nat. Acad. Sci. U.S.A.*, 78, pp. 2848–2852 (1981)]. The hybrids obtained consisted of the four possible combinations of gene fragments developed upon finding that two of the eight human (cDNA-derived) genes fortuitously included only once within the sequence, base sequences corresponding to the restriction endonuclease cleavage sites for the bacterial endonucleases, PvuII and BglII.

There exists, therefore, a substantial need in the art for more efficient procedures for the total synthesis from nucleotide bases of manufactured DNA sequences coding for large polypeptides such as the interferons. There additionally exists a need for synthetic methods which will allow for the rapid construction of variant forms of synthetic sequences such as will permit the microbial expression of synthetic polypeptides which vary from naturally occurring forms in terms of the identity and/or position of one or more selected amino acids.

BRIEF SUMMARY

The present invention provides novel, rapid and highly efficient procedures for the total synthesis of linear, double stranded DNA sequences in excess of about 200 nucleotide base pairs in length, which sequences may comprise entire structural genes capable of directing the synthesis of a wide variety of polypeptides of interest.

According to the invention, linear, double stranded DNA sequences of a length in excess of about 200 base pairs and coding for expression of a predetermined continuous sequence of amino acids within a selected host microorganism transformed by a selected DNA vector including the sequence, are synthesized by a method comprising:

(a) preparing two or more different, subunit, linear, double stranded DNA sequences of about 100 or more base pairs in length for assembly in a selected assembly vector, each different subunit DNA sequence prepared comprising a series of nucleotide base codons coding for a different continuous portion of said predetermined sequence of amino acids to be expressed, one terminal region of a first of said subunits comprising a portion of a base sequence which provides a recognition site for cleavage by a first restriction endonuclease, which recognition site is entirely present either once or not at all in said selected assembly vector upon insertion of the subunit therein, one terminal region of a second of said subunits comprising a portion of a base sequence which provides a recognition site for cleavage by a second restriction endonuclease other than said first endonuclease, which recognition site is entirely present once or not at all in said selected assembly vector upon insertion of the subunit therein, at least one-half of all remaining terminal regions of subunits comprising a portion of a recognition site (preferably a palindromic six base recognition site) for cleavage by a restriction endonuclease other than said first and second endonucleases, which recognition site is entirely present once and only once in said selected assembly vector after insertion of all subunits thereinto; and (b) serially inserting each of said subunit DNA sequences prepared in step (a) into the selected assembly vector and effecting the biological amplification of the assembly vector subsequent to each insertion, is thereby to form a DNA vector including the desired DNA sequence coding for the predetermined continuous amino acid sequence and wherein the desired DNA sequence assembled includes at least one unique, preferably palindromic six base, recognition site for restriction endonuclease cleavage at an intermediate position therein.

The above general method preferably further includes the step of isolating the desired DNA sequence from the assembly vector preferably to provide one of the class of novel manufactured DNA sequences having at least one unique palindromic six base recognition site for restriction endonuclease cleavage at an intermediate position therein. A sequence so isolated may then be inserted in a different, "expression" vector and direct expression of the desired polypeptide by a microorganism which is the same as or different from that in which the assembly vector is amplified. In other preferred embodiments of the method: at least three different subunit DNA sequences are prepared in step (a) and serially inserted into said selected assembly vector in step (b) and the desired manufactured DNA sequence obtained includes at least two unique palindromic six base recognition sites for restriction endonuclease cleavage at intermediate positions therein; the DNA sequence synthesized comprises an entire structural gene coding for a biologically active polypeptide; and, in the DNA sequence manufactured, the sequence of nucleotide bases includes one or more codons selected, from among alternative codons specifying the same amino acid, on the basis of preferential expression characteristics of the codon in said selected host microorganism.

Novel products of the invention include manufactured, linear, double stranded DNA sequences of a length in excess of about 200 base pairs and coding for the expression of a predetermined continuous sequence of amino acids by a selected host microorganism transformed with a selected DNA vector including the sequence, characterized by having at least one unique palindromic six base recognition site for restriction endonuclease cleavage at an intermediate position therein. Also included are polypeptide products of the expression by an organism of such manufactured sequences.

Illustratively provided by the present invention are novel manufactured genes coding for the synthesis of human immune interferon (IFN-$\gamma$) and novel biologically functional analog polypeptides which differ from human immune interferon in terms of the identity and/or location of one or more amino acids. Also provided are manufactured genes coding for synthesis of human leukocyte interferon of the F subtype ("LeIFN-F" or "IFN-$\alpha$F") and analogs thereof, along with consensus human leukocyte interferons.

DNA subunit sequences for use in practice of the methods of the invention are preferably synthesized from nucleotide bases according to the methods disclosed in co-owned, concurrently-filed U.S. patent application Ser. No. 375,493, by Yitzhak Stabinsky, entitled "Manufacture and Expression of Structural Genes". Briefly summarized the general method comprises the steps of:

(1) preparing two or more different, linear, duplex DNA strands, each duplex strand including a double stranded region of 12 or more selected complementary base pairs and further including a top single stranded terminal sequence of from 3 to 7 selected bases at one end of the strand and/or a bottom single stranded terminal sequence of from 3 to 7 selected bases at the other end of the strand, each single stranded terminal sequence of each duplex DNA strand comprising the entire base complement of at most one single stranded terminal sequence of any other duplex DNA strand prepared; and (2) annealing each duplex DNA strand prepared in step (1) to one or two different duplex strands prepared in step (1) having a complementary single stranded terminal sequence, thereby to form a single continuous double stranded DNA sequence which has a duplex region of at least 27 selected base pairs including at least 3 base pairs formed by complementary association of single stranded terminal sequences of duplex DNA strands prepared in step (1) and which has from 0 to 2 single stranded top or bottom terminal regions of from 3 to 7 bases.

In the preferred general process for subunit manufacture, at least three different duplex DNA strands are prepared in step (1) and all strands so prepared are annealed concurrently in a single annealing reaction mixture to form a single continuous double stranded DNA sequence which has a duplex region of at least 42 selected base pairs including at least two non-adjacent sets of 3 or more base pairs formed by complementary association of single stranded terminal sequences of duplex strands prepared in step (1).

The duplex DNA strand preparation step (1) of the preferred subunit manufacturing process preferably comprises the steps of:

(a) constructing first and second linear deoxyoligonucleotide segments having 15 or more bases in a selected linear sequence, the linear sequence of bases of the second segment comprising the total complement of the sequence of bases of the first segment except that at least one end of the second segment shall either include an additional linear sequence of from 3 to 7 selected bases beyond those fully complementing the first segment, or shall lack a linear sequence of from 3 to 7 bases complementary to a terminal sequence of the first segment, provided, however, that the second segment shall not have an additional sequence of bases or be lacking a sequence of bases at both of its ends; and, (b) combining the first and second segments under conditions conducive to complementary association between segments to form a linear, duplex DNA strand.

The sequence of bases in the double stranded DNA subunit sequences formed preferably includes one or more triplet codons selected from among alternative codons specifying the same amino acid on the basis of preferential expression characteristics of the codon in a projected host microorganism, such as yeast cells or bacteria, especially *E. coli* bacteria.

Also provided by the present invention are improvements in methods and materials for enhancing levels of expression of selected exogenous genes in *E. coli* host cells. Briefly stated, expression vectors are constructed to include selected DNA sequences upstream of polypeptide coding regions which selected sequences are duplicative of ribosome binding site sequences extant in genomic *E. coli* DNA associated with highly expressed endogenous polypeptides. A presently preferred selected sequence is duplicative of the ribosome binding site sequence associated with *E. coli* expression of outer membrane protein F ("OMP-F").

Other aspects and advantages of the present invention will be apparent upon consideration of the following detailed description thereof.

DETAILED DESCRIPTION

As employed herein, the term "manufactured" as applied to a DNA sequence or gene shall designate a product either totally chemically synthesized by assembly of nucleotide bases or derived from the biological replication of a product thus chemically synthesized. As such, the term is exclusive of products "synthesized" by cDNA methods or genomic cloning methodologies which involve starting materials which are of biological origin. Table I below sets out abbreviations employed herein to designate amino acids and includes IUPAC-recommended single letter designations.

TABLE I

| Amino Acid | Abbreviation | IUPAC Symbol |
|---|---|---|
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

The following abbreviations shall be employed for nucleotide bases: A for adenine; G for guanine; T for thymine; U for uracil; and C for cytosine. For ease of understanding of the present invention, Table II and II below provide tabular correlations between the 64 alternate triplet nucleotide base codons of DNA and the 20 amino acids and transcription termination ("stop") functions specified thereby. In order to determine the corresponding correlations for RNA, U is substituted for T in the tables.

TABLE II

| FIRST POSITION | SECOND POSITION | | | | THIRD POSITION |
|---|---|---|---|---|---|
| | T | C | A | G | |
| T | Phe | Ser | Tyr | Cys | T |
| | Phe | Ser | Tyr | Cys | C |
| | Leu | Ser | Stop | Stop | A |
| | Leu | Ser | Stop | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val | Ala | Glu | Gly | G |

TABLE III

| Amino Acid | | Specifying Codon(s) |
|---|---|---|
| (A) | Alanine | GCT, GCC, GCA, GCG |
| (C) | Cysteine | TGT, TGC |
| (D) | Aspartic acid | GAT, GAC |
| (E) | Glutamic acid | GAA, GAG |
| (F) | Phenylalanine | TTT, TTC |
| (G) | Glycine | GGT, GGC, GGA, GGG |
| (H) | Histidine | CAT, CAC |
| (I) | Isoleucine | ATT, ATC, ATA |
| (K) | Lysine | AAA, AAG |
| (L) | Leucine | TTA, TTG, CTT, CTC, CTA, CTG |
| (M) | Methionine | ATG |
| (N) | Asparagine | AAT, AAC |
| (P) | Proline | CCT, CCC, CCA, CCG |
| (Q) | Glutamine | CAA, CAG |
| (R) | Arginine | CGT, CGC, CGA, CGG, AGA, AGG |
| (S) | Serine | TCT, TCC, TCA, TCG, AGT, AGC |
| (T) | Threonine | ACT, ACC, ACA, ACG |
| (V) | Valine | GTT, GTC GTA, GTG |
| (W) | Tryptophan | TGG |
| (Y) | Tyrosine | TAC, TAT |
| STOP | | TAA, TAG, TGA |

A "palindromic" recognition site for restriction endonuclease cleavage of double stranded DNA is one which displays "left-to-right and right-to-left" symmetry between top and bottom base complements, i.e., where "readings" of complementary base sequences of the recognition site from 5' to 3' ends are identical. Examples of palindromic six base recognition sites for restriction endonuclease cleavage include the sites for cleavage by HindIII wherein top and bottom strands read from 5' to 3' as AAGCTT. A non-palindromic six base restriction site is exemplified by the site for cleavage by EcoP15, the top strand of which reportedly reads CAGCAG. The bottom strand base complement, when read 5' to 3' is CTGGTG. Essentially by definition, restriction sites comprising odd numbers of bases (e.g., 5, 7) are non-palindromic. Certain endonucleases will cleave at variant forms of a site, which may be palindromic or not. For example, XhoII will recognize a site which reads (any purine) GATC (any pyrimidine) including the palindromic sequence AGATCT and the non-palindromic sequence GGATCT. Referring to the previously-noted "BRL Restriction Endonuclease Reference Chart," endonucleases recognizing six base palindromic sites exclusively include BbrI, ChuI, Hin173, Hin91R, HinbIII, HinbIII, HindIII, HinfII, HsuI, BglII, StuI, RruI, ClaI, AvaIII, PvuII, SmaI, XmaI, EccI, SacII, SboI, SbrI, ShyI, SstII, TglI, AvrII, PvuI, RshI, RspI, XniI, XorII, XmaIII, BluI, MsiI, ScuI, SexI, SgoI, SlaI, SluI, SpaI, XhoI, XpaI, Bce170, Bsu1247, PstI, SalPI, XmaII, XorI, EcoRI, Rsh630I, SacI, SstI, SphI, BamHI, BamKI, BamNI, BamFI, BstI, KpnI, SalI, XamI, HpaI, XbaI, AtuCI, BclI, CpeI, SstIV, AosI, MstI, BalI, AsuII, and MlaI. Endonucleases which recognize only non-palindromic six base sequences exclusively include Tth111II, EcoP15, AvaI, and AvrI. Endonucleases-recognizing both palindromic and non-palindromic six base sequences include HaeI, HgiAI, AcyI, AosII, AsuIII, AccI, CbuII, HincII, HindII, MnnI, XhoII, BaeII, HinHI, NgoI, and EcoRI'.

Upon determination of the structure of a desired polypeptide to be produced, practice of the present invention involves: preparation of two or more different specific, continuous double stranded DNA subunit sequences of 100 or more base pairs in length and having terminal portions of the proper configuration; serial insertion of subunits into a selected assembly vector with intermediate amplification of the hybrid vectors in a selected host organism; use of the assembly vector (or an alternate, selected "expression" vector including the DNA sequence which has been manufactured from the subunits) to transform a suitable, selected host; and, isolating polypeptide sequences expressed in the host organism. In its most efficient forms, practice of the invention involves using the same vector for assembly of the manufactured sequence and for large scale expression of the polypeptide. Similarly, the host microorganism employed for expression will ordinarily be the same as employed for amplifications performed during the subunit assembly process.

The manufactured DNA sequence may be provided with a promoter/regulator region for autonomous control of expression or may be incorporated into a vector in a manner providing for control of expression by a promoter/regulator sequence extant in the vector. Manufactured DNA sequences of the invention may suitably be incorporated into existing plasmid-borne genes (e.g., β-galactosidase) to form fusion genes coding for fusion polypeptide products including the desired amino acid sequences coded for by the manufactured DNA sequences.

In practice of the invention in its preferred forms, polypeptides produced may vary in size from about 65 or 70 amino acids up to about 200 or more amino acids. High levels of expression of the desired polypeptide by selected transformed host organisms is facilitated through the manufacture of DNA sequences which include one or more alternative codons which are preferentially expressed by the host.

Manufacture of double stranded subunit DNA sequences of 100 to 200 base pairs in length may proceed according to prior art assembly methods previously referred to, but is preferably accomplished by means of the rapid and efficient procedures disclosed in the aforementioned U.S. application Ser. No. 375,493 by Stabinsky and used in certain of the following examples of actual practice of the present invention. Briefly put, these procedures involve the assembly from deoxyoligonucleotides of two or more different, linear, duplex DNA strands each including a relatively long double stranded region along with a relatively short single stranded region on one or both opposing ends of the double strand. The double stranded regions are designed to include codons needed to specify assembly of an initial, or terminal or intermediate portion of the total amino acid sequence of the desired polypeptide. Where possible, alternative codons preferentially expressed by a projected host (e.g., *E. coli*) are employed. Depending on the relative position to be assumed in the finally assembled subunit DNA sequence, the single stranded region(s) of the duplex strands will include a sequence of bases which, when complemented by bases of other duplex strands, also provide codons specifying amino acids within the desired polypeptide sequence.

Duplex strands formed according to this procedure are then enzymatically annealed to the one or two different duplex strands having complementary short, single stranded regions to form a desired continuous double stranded subunit DNA sequence which codes for the desired polypeptide fragment.

High efficiencies and rapidity in total sequence assembly are augmented in such procedures by performing a single annealing reaction involving three or more duplex strands, the short, single stranded regions of which constitute the base complement of at most one other single stranded region of any other duplex strand. Providing all duplex strands formed with short single stranded regions which uniquely complement only one of the single stranded regions of any other duplex is accomplished by alternative codon selection within the context of genetic code redundancy, and preferably also in the context of codon preferences of the projected host organism.

The following description of the manufacture of a hypothetical long DNA sequence coding for a hypothetical polypeptide will serve to graphically illustrate practice of the invention, especially in the context of formation of proper terminal sequences on subunit DNA sequences.

A biologically active polypeptide of interest is isolated and its amino acids are sequenced to reveal a constitution of 100 amino acid residues in a given continuous sequence. Formation of a manufactured gene for microbial expression of the polypeptide will thus require assembly of at least 300 base pairs for insertion into a selected viral or circular plasmid DNA vector to be used for transformation of a selected host organism.

A preliminary consideration in construction of the manufactured gene is the identity of the projected microbial host, because foreknowledge of the host allows for codon selection in the context of codon preferences of the host species. For purposes of this discussion, the selection of an *E. coli* bacterial host is posited.

A second consideration in construction of the manufactured gene is the identity of the projected DNA vector employed in the assembly process. Selection of a suitable vector is based on existing knowledge of sites for cleavage of the vector by restriction endonuclease enzymes. More particularly, the assembly vector is selected on the basis of including DNA sequences providing endonuclease cleavage sites which will permit easy insertion of the subunits. In this regard, the assembly vector selected preferably has at least two restriction sites which occur only once (i.e., are "unique") in the vector prior to performance of any subunit insertion processes. For the purposes of this description, the selection of a hypothetical circular DNA plasmid pBR 3000 having a single EcoRI restriction site, i.e.,

-GAATTC-, -CTTAAGand a single PvuII restriction site, i.e.,

-CAGCTG-, -GTCGACis posited.

The amino acid sequence of the desired polypeptide is then analyzed in the context of determining availability of alternate codons for given amino acids (preferably in the context of codon preferences of the projected *E. coli* host). With this information in hand, two subunit DNA sequences are designed, preferably having a length on the order of about 150 base pairs—each coding for approximately one-half of the total amino acid sequences of the desired polypeptide. For purposes of this description, the two subunits manufactured will be referred to as "A" and "B".

The methods of the present invention as applied to two such subunits, generally call for: insertion of one of the subunits into the assembly vector; amplification of the hybrid vector formed; and insertion of the second subunit to form a second hybrid including the assembled subunits in the proper sequence. Because the method involves joining the two subunits together in a manner permitting the joined ends to provide a continuous preselected sequence of bases coding for a continuous preselected sequence of amino acids, there exist certain requirements concerning the identity and sequence of the bases which make up the terminal regions of the manufactured subunits which will be joined to another subunit. Because the method calls for joining subunits to the assembly vector, there exist other requirements concerning the identity and sequence of the bases which make up those terminal regions of the manufactured subunits which will be joined to the assembly vector. Because the subunits are serially, rather than concurrently, inserted into the assembly vector (and because the methods are most beneficially practiced when the subunits can be selectively excised from assembled form to allow for alterations in selected base sequences therein), still further requirements exist concerning the identity of the bases in terminal regions of subunits manufactured. For ease of understanding in the following discussion of terminal region characteristics, the opposing terminal regions of subunits A and B are respectively referred to as A-1 and A-2, and B-1 and B-2, viz:

| B-2 | B-1 | A-2 | A-1 |
|---|---|---|---|
| | B | | A |

Assume that an assembly strategy is developed wherein subunit A is to be inserted into pBR3000 first, with terminal region A-1 to be ligated to the vector at the EcoRI restriction site. In the simplest case, the terminal region is simply provided with an EcoRI "sticky end", i.e., a single strand of four bases (-AATT- or -TTAA-) which will complement a single stranded sequence formed upon EcoRI digestion of pBR3000. This will allow ligation of terminal region A-1 to the vector upon treatment with ligase enzyme. Unless the single strand at the end of terminal region A-1 is preceded by an appropriate base pair (e.g.

5'-G-
3'-CTTAA-), the entire recognition site will not be reconstituted upon ligation to the vector. Whether or not the EcoRI recognition site is reconstituted upon ligation (i.e., whether or not there will be 0 or 1 EcoRI sites remaining after insertion of subunit A into the vector) is at the option of the designer of the strategy. Alternatively, one may construct the terminal region A-1 of subunit A to include a complete set of base pairs providing a recognition site for some other endonuclease, hypothetically designated "XXX", and then add on portions of the EcoRI recognition site as above to provide an EcoRI "linker". To be of practical use in excising subunit A from an assembled sequence, the "XXX" site should not appear elsewhere in the hybrid plasmid formed upon insertion. The requirement for construction of terminal region A-1 is, therefore, that it comprise a portion (i.e., all or part) of a base sequence which provides a recognition site for cleavage by a restriction endonuclease, which recognition site is entirely present either once or not at all in the assembly vector upon insertion of the subunit.

Assume that terminal region B-2 of subunit B is also to be joined to the assembly vector (e.g., at the single recognition site for PvuII cleavage present on pBR3000). The requirements for construction of terminal region B-2 are the same as for construction of A-1, except that the second endonuclease enzyme in reference to which the construction of B-2 is made must be different from that with respect to which the construction of A-1 is made. If recognition sites are the same, one will not be able to separately excise segments A and B from the fully assembled sequence.

The above assumptions require, then, that terminal region A-2 is to be ligated to terminal region B-1 in the final pBR3000 hybrid. Either the terminal region A-2 or the terminal region B-1 is constructed to comprise a portion of a (preferably palindromic six base) recognition site for restriction endonuclease cleavage by hypothetical third endonuclease "YYY" which recognition site will be entirely present once and only once in the expression vector upon insertion of all subunits thereinto, i.e., at an intermediate position in the assemblage of subunits. There exist a number of strategies for obtaining this result. In one alternative strategy, the entire recognition site of "YYY" is contained in terminal region A-2 and the region additionally includes the one or more portions of other recognition sites for endonuclease cleavage needed to (1) complete the insertion of subunit A into the assembly vector for amplification purposes, and (2) allow for subsequent joining of subunit A to subunit B. In this case, terminal region B-1 would have at its end only the bases necessary to link it to terminal region A-2. In another alternative, the entire "YYY" recognition site is included in terminal region B-1 and B-1 further includes at its end a portion of a recognition site for endonuclease cleavage which is useful for joining subunit A to subunit B.

As another alternative, terminal region B-1 may contain at its end a portion of the "YYY" recognition site. Terminal region A-2 would then contain the entire "YYY" recognition site plus, at its end, a suitable "linker" for joining A-2 to the assembly vector prior to amplification of subunit A (e.g., a PvuII "sticky end"). After amplification of the hybrid containing subunit A, the hybrid would be cleaved with "YYY" (leaving a sticky-ended portion of the "YYY" recognition site exposed on the end of A-2) and subunit B could be inserted with its B-1 terminal region joined with the end of terminal region A-2 to reconstitute the entire "YYY" recognition site. The requirement for construction of the terminal regions of all segments (other than A-1 and B-2) is that one or the other or both (i.e., "at least half") comprise a portion (i.e., include all or part) of a recognition site for third restriction endonuclease cleavage, which recognition site is entirely present once and only once (i.e., is "unique") in said assembly vector after insertion of all subunits thereinto. To generate a member of the class of novel DNA sequences of the invention, the recognition site of the third endonuclease should be a six base palindromic recognition site.

While a subunit "terminal region" as referred to above could be considered to extend from the subunit end fully halfway along the subunit to its center, as a practical matter the constructions noted would ordinarily be performed in the final 10 or 20 bases. Similarly, while the unique "intermediate" recognition site in the two subunit assemblage may be up to three times closer to one end of the manufactured sequence than it is to the other, it will ordinarily be located near the center of the sequence. If, in the above description, a synthetic plan was generated calling for preparation of three subunits to be joined, the manufactured gene would include two unique restriction enzyme cleavage sites in intermediate positions at least one of which will have a palindromic six base recognition site in the class of new DNA sequences of the invention.

The significant advantages of the above-described process are manifest. Because the manufactured gene now includes one or more unique restriction endonuclease cleavage sites at intermediate positions along its length, modifications in the codon sequence of the two subunits joined at the cleavage site may be effected with great facility and without the need to re-synthesize the entire manufactured gene.

Following are illustrative examples of the actual practice of the invention in formation of manufactured genes capable of directing the synthesis of: human immune interferon (IFNγ) and analogs thereof; human leukocyte interferon of the F subtype (INF-αF) and analogs thereof; and, multiple consensus leukocyte interferons which, due to homology to IFN-αF can be named as IFN-αF analogs. It will be apparent from these examples that the gene manufacturing methodology of the present invention provides an overall synthetic strategy for the truly rapid, efficient synthesis and expression of genes of a length in excess of 200 base pairs within a highly flexible framework allowing for variations in the structures of products to be expressed which has not heretofore been available to investigators practicing recombinant DNA techniques.

EXAMPLE 1

In the procedure for construction of synthetic genes for expression of human IFNγ a first selection made was the choice of E. coli as a microbial host for eventual expression of the desired polypeptides. Thereafter, codon selection procedures were carried out in the context of E. coli codon preferences enumerated in the Grantham publications, supra. A second selection made was the choice of pBR322 as an expression vector and, significantly, as the assembly vector to be employed in amplification of subunit sequences. In regard to the latter factor, the plasmid was selected with the knowledge that it included single BamHI, HindIII, and SalI restriction sites. With these restriction sites and the known sequence of amino acids in human immune interferon in mind, a general plan for formation of three "major" subunit DNA sequences (IF-3, IF-2 and IF-1) and one "minor" subunit DNA sequence (IF-4) was evolved. This plan is illustrated by Table IV below.

TABLE IV

```
IF-4

HpaI                                                            -1   1   2   3   4   BamHI
                                                                Met Cys Tyr Cys Gln
        ─────────a─────────       ─────────c─────────       ─────────e─────────
  A ACT AGT ACG CAA GTT CAC   GTA AAA AGG GTA TCG ACA   ATG TGT TAC TGC CAG
  T TGA TCA TGC GTT CAA GTG   CAT TTT TCC CAT AGC TGT   TAC ACA ATG ACG GTC CTAG
        ─────────b─────────       ─────────d─────────       ─────────f─────────
```

TABLE IV-continued

IF-3

```
                    4                           10
EcoRI           Gln Asp Pro Tyr Val Lys Glu Ala Glu Asn Leu Lys Lys Tyr Phe Asn
                ┌─────── 43 ────────┐           ┌─────── 41 ────────┐
  A ATT CGA CAG│GAT CCG TAC GTT AAG GAA GCA GAA AAC CTG AAA AAA TAC TTC AAC
    GCT GTC CTA│GGC ATG CAA TTC CTT CGT CTT TTG GAC TTT TTT ATG AAG TTG
               └─────── 44 ────────┘           └─────── 42 ────────┘
          BamHI 20                                30
Ala Gly His Ser Asp Val Ala Asp Asn Gly Thr Leu Phe Leu Gly Ile Leu Lys Asn Trp
┌─────── 39 ────────┐   ┌─────── 37 ────────┐   ┌─────── 35 ────────┐
GCA GGC CAC TCC GAC GTA GCT GAT AAC GGC ACC CTG TTC CTG GGT ATC CTA AAA AAC TGG
CGT CCG GTG AGG CTG CAT CGA CTA TTG CCG TGG GAC AAG GAC CCA TAG GAC TTT TTG ACC
        └─────── 40 ────────┘   └─────── 38 ────────┘   └─────── 36 ────────┘

40                      50       53
Lys Glu Glu Ser Asp Arg Lys Ile Met Gln Ser Gln Ile Val    HindIII
┌─────── 33 ────────┐         ┌─────── 31 ────────┐
AAA GAG GAA TCC GAC CGT AAG ATC ATG CAG TCT CAA ATT GTA
TTT CAC CTT AGG CTG GCA TTC TAG TAC GTC AGA GTT TAA CAT TCG A
       └─────── 34 ────────┘         └─────── 32 ────────┘
```

IF-2

EcoRI

```
                   54                        60                       70
            Val Ser Phe Tyr Phe Lys Leu Phe Lys Asn Phe Lys Asp Asp Gln Ser Ile Gln
            ┌─── 29 ───┐        ┌─── 27 ──┐         ┌─── 25 ───┐
AATT CAG GTA│AGC TTC TAC TTC AAA CTG TTC AAG AAC TTC AAA GAC GAT CAA TCC ATC CAG
    GTC CAT TCG│AAG ATG AAG TTT GAC AAG TTC TTG AAG TTT CTG CTA GTT AGG TAG GTC
           └── 30 ──┘          └── 28 ──┘          └── 26 ──┘
          HindIII 80                                90
Lys Ser Val Glu Thr Ile Lys Glu Asp Met Asn Val Lys Phe Phe Asn Ser Asn Lys Lys
┌─── 23 ───┐       ┌── 21 ──┐        ┌── 19 ──┐
AAG AGC GTA GAA ACT ATT AAG GAG GAC ATG AAC GTA AAA TTC TTT AAC AGC AAC AAG AAG
TTC TCG CAT CTT TGA TAA TTC CTC CTG TAC TTG CAT TTT AAG AAA TTG TCG TTG TTC TTC
        └── 24 ──┘         └── 22 ──┘         └── 20 ──┘
                                       100          BglII
Lys Arg Asp Asp Phe Glu Lys Leu Thr Asn Tyr Ser Val Thr
       ┌── 17 ──┐            ┌── 15 ──┐
AAA CGC GAT GAC TTC GAG AAA CTG ACT AAC TAC TCT GTT ACA
TTT GCG CTA CTG AAG CTC TTT GAC TGA TTG ATG AGA CAA TGT CTA G
        └── 18 ──┘            └── 16 ──┘
```

IF-1

EcoRI

```
                   105              110
            Leu Asn Val Gln Arg Lys Ala Ile His Glu Glu Ile Gln Val
            Asp
            ┌─── 13 ───┐    ┌─── 11 ───┐    ┌──── 9 ────┐
  A ATT CAG GCA│GAT CTG AAC GTG CAG CGT AAA GCT ATT CAC GAA CTG ATC CAA GTT
       GTC CGT CTA│GAC TTG CAC GTC CGA TTT CGA TAA GTG CTT GAC TAG GTT CAA
              └── 14 ──┘    └── 12 ──┘    └── 10 ──┘
          BglII 120                          130
Met Ala Glu Leu Ser Pro Ala Ala Lys Thr Gly Lys Arg Lys Arg Ser Gln Met Leu Phe
        ┌── 7 ──┐          ┌── 5 ──┐          ┌── 3 ──┐
ATG GCT GAA CTG TCT CCT GCG GCA AAG ACT GGC AAA CGC AAG CGT AGC CAG ATG CTG TTT
TAC CGA CTT GAC AGA GGA CGC CGT TTC TGA CCG TTT GCG TTC GCA TCG GTC TAC GAC AAA
         └── 8 ──┘          └── 6 ──┘

┌───┬───┐               146    SalI
│140│140│
│Arg│Gln│Gly Arg Arg Ala Ser Gln Stop
├───┼───┤        ┌── 1 ──┐
│CGT│CAG│GGT CGC CGT GCT TCT CAG TGA TAG
│GCA│GTC│CCA GCG GCA CGA AGA GTC ACT ATC AGC T
└───┴───┘ └── 4 ──┘     └── 2 ──┘
```

The "minor" sequence (IF-4) is seen to include codons for the 4th through 1st (5'-TGT TAC TGC CAG) amino acids and an ATG codon for an initiating methionine [Met$^{-1}$]. In this construction, it also includes additional bases to provide a portion of a control involved in an expression vector assembly from pBR 322 as described infra.

Alternative form of subunit IFN-1 for use in synthesis of a manufactured gene for [Arg$^{140}$]IFNγ included the codon 5'-CGT in place of 5'-CAG (for [Gln$^{140}$]) at the codon site specifying the 140th amino acid.

The codon sequence plan for the top strand of the polypeptide-specifying portion total DNA sequence synthesized was as follows:

5'-TGT-TAC-TGC-CAG-GAT-CCG-TAC-GTT-AAG-GAA-GCA-

GAA-AAC-CTG-AAA-AAA-TAC-TTC-AAC-GCA-GGC-CAC-TCC-

GAC-GTA-GCT-GAT-AAC-GGC-ACC-CTG-TTC-CTG-GGT-ATC-

CTA-AAA-AAC-TGG-AAA-GAG-GAA-TCC-GAC-CTG-AAG-ATC-

ATG-CAG-TCT-CAA-ATT-GTA-AGC-TTC-TAC-TTC-AAA-CTG-

TTC-AAG-AAC-TTC-AAA-GAC-GAT-CAA-TCC-ATC-CAG-AAG-

AGC-GTA-GAA-ACT-ATT-AAG-GAG-GAC-ATG-AAC-GTA-AAA-

TCC-TTT-AAC-AGC-AAC-AAG-AAG-AAA-CGC-GAT-GAC-TTC-

GAG-AAA-CTG-ACT-AAC-TAC-TCT-GTT-ACA-GAT-CTG-AAC-

GTG-CAG-CGT-AAA-GCT-ATT-CAC-GAA-CTG-ATC-CAA-GTT-

ATG-GCT-GAA-CTG-TCT-CCT-GCG-GCA-AAG-ACT-GGC-AAA-

CGC-AAG-CGT-AGC-CAG-ATG-CTG-TTT-CAG-[or CGT]-

CGT-CGC-CGT-GCT-TCT-CAG.

In the above sequence, the control sequence bases and the initial methionine-specifying codon is not illustrated, nor are termination sequences or sequences providing a terminal SalI restriction site. Vertical lines separate top strand portions attributable to each of the subunit sequences.

The following example illustrates a preferred general procedure for preparation of deoxyoligonucleotides for use in the manufacture of DNA sequences of the invention.

EXAMPLE 2

Oligonucleotide fragments were synthesized sing a four-step procedure and several intermediate washes. Polymer bound dimethoxytrityl protected nucleoside in a sintered glass funnel was first stripped of its 5'-protecting group (dimethoxytrityl) using 3% trichloroacetic acid in dichloromethane for 1½ minutes. The polymer was then washed with methanol, tetrahydrofuran and acetonitrile. The washed polymer was then rinsed with dry acetonitrile, placed under argon and then treated in the condensation step as follows. 0.5 ml of a solution of 10 mg tetrazole in acetonitile was added to the reaction vessel containing polymer. Then 0.5 ml of 30 mg protected nucleoside phosphoramidite in acetronitrile was added. This reaction was agitated and allowed to react for 2 minutes. The reactants were then removed by suction and the polymer rinsed with acetonitrile. This was followed by the oxidation step wherein 1 ml of a solution containing 0.1 molar $I_2$ in 2–6-lutidine/$H_2O$/THF, 1:2:2, was reacted with the polymer bound oligonucleotide chain for 2 minutes. Following a THF rinse capping was done using a solution of dimethylaminopyridine (6.5 g in 100 ml THF) and acetic anhydride in the proportion 4:1 for 2 minutes. This was followed by a methanol rinse and a THF rinse. Then the cycle began again with a trichloroacetic acid in $CH_2Cl_2$ treatment. The cycle was repeated until the desired oligonucleotide sequence was obtained.

The final oligonucleotide chain was treated with thiophenol dioxane, triethylamine 1:2:2, for 45 minutes at room temperature. Then, after rinsing with dioxane, methanol and diethylether, the oligonucleotide was cleaved from the polymer with concentrated ammonium hydroxide at room temperature. After decanting the solution from the polymer, the concentrated ammonium hydroxide solution was heated at 60° C. for 16 hours in a sealed tube.

Each oligonucleotide solution was then extracted four times with 1-butanol. The solution was loaded into a 20% polyacrylamide 7 molar urea electrophoresis gel and, after running, the appropriate product DNA band was isolated.

Subunits were then assembled from deoxyoligonucleotides according to the general procedure for assembly of subunit IF-1.

Following the isolation of the desired 14 DNA segments, subunit IF-1 was constructed in the following manner:

1. One nanomole of each of the DNA fragments excluding segment 13 and segment 2 which contain 5' cohesive ends, were subjected to 5'-phosphorylation;

2. The complementary strands of DNA, segments 13 and 14, 11 and 12, 9 and 10, 7 and 8, 5 and 6, 3 and 4 and 1 and 2 were combined together, warmed to 90° and slowly cooled to 25°;

3. The resulting annealed pairs of DNA were combined sequentially and warmed to 37° and slowly cooled to 25°;

4. The concentration of ATP and DTT in the final tube containing segments 1 thru 14 was adjusted to 150 μM and 18 he respectively. Twenty units of T-4 DNA ligase was added to this solution and the reaction was incubated at 4° for 18 hrs;

5. The resulting crude product was heated 90° for 2 min. and subjected to gel filtration on Sephadex G50/40 using 10 mM triethyl ammonium bicarbonate as the eluent;

6. The desired product was purifier, following 5' phosphorylation, using an 8% polyacrylamide-TBE gel.

Subunits IF-2, IF-3 and IF-4 were constructed in a similar manner.

The following example relates to: assembly of the complete human immune interferon gene from subunits IF-1, IF-2, IF-3, and IF-4; procedures for the growing, under appropriate nutrient conditions, of transformed *E. coli* cells, the isolation of human immune interferon from the cells, and the testing of biological activity of interferon so isolated.

EXAMPLE 3

The major steps in the general procedure for assembly of the complete human IFNγ specifying genes from subunits IF-1, IP-2, and IF-3 are illustrated in FIG. 1.

The 136 base pair subunit IF-1 was electro-eluted from the gel, ethanol precipitated and resuspended in water at a concentration of 0.05 pmol/μl. Plasmid pBR322 (2.0 pmol) was digested with EcoRI and SalI, treated with phosphatase, phenol extracted, ethanol precipitated, and resuspended in water at a concentration of 0.1 pmol/μl. Ligation was carried out with 0.1 pmol of the plasmid and 0.2 pmol of subunit IF-1, using T-4 DNA ligase to form hybrid plasmid pINT1.

*E. coli* were transformed and multiple copies of pINT1 were isolated therefrom.

The above procedure was repeated for purposes of inserting the 153 base pair subunit IF-2 to form pINF2 except that the plasmid was digested with EcoRI and BglII. The 153 base pair IF-3 subunit was similarly inserted into pINT2 during manufacture of pINT3 except that EcoRI and Hind III were used to digest the plasmid.

An IF-4 subunit was employed in the construction of the final expression vector as follows: Plasmid PVvI was purchased from Stanford University, Palo Alto, Calif., and digested with PvuII. Using standard procedures, an EcoRI recognition site was inserted in the plasmid at a PvuII site. Copies of this hybrid were then digested with EcoRI and HpaI to provide a 245 base pair sequence including a portion of the trp promoter/operator region. By standard procedures, IF-4 was added to the HpaI site in order to incorporate the remaining 37 base pairs of the complete trp translational initiation signal and bases providing codons for the initial four amino acids of immune interferon (Cys-Tyr-Cys-Gln). The resulting assembly was then inserted into pINT3 which had been digested with EcoRI and BamHI to yield a plasmid designated pINTγ-trpI7.

*E. coli* cells containing pINTγ-trpI7 were grown on K media in the absence of tryptophan to an O.D.$_{.600}$ of 1. Indoleacrylic acid was added at a concentration of 20 µq per ml and the cells were cultured for an additional 2 hours at 37° C. Cells were harvested by centrifugation and the cell pellet was resuspended in fetal calf serum buffered with HEPES (pH 8.0). Cells were lysed by one passage through a French press at 10,000 psi. The cell lysate was cleared of debris by centrifugation and the supernatant was assayed for antiviral activity by the CPE assay ["The Interferon System" Stewart, ed., Springer-Verlag, N.Y., N.Y. (1981)). The isolated product of expression was designated γ-1.

This example relates to a modification in the DNA sequence of plasmid pINTγ-trpI7 which facilitated the use of the vector in the trp promoter-controlled expression of structural genes coding for, e.g., analogs of IFN-γ and IFN-αF.

EXAMPLE 4

Segment IF-4, as previously noted, had been constructed to include bases coding for an initial methionine and the first four amino acids of IFN-γ as well as 37 base pairs (commencing at its 5' end with a HpaI blunt end) which completed at the 3' end of a trp promoter/operator sequence, including a Shine Delgarno ribosome binding sequence. It was clear that manipulations involving sequences coding IFN-γ analogs and for polypeptides other than IFN-γ would be facilitated if a restriction site 3' to the entire trp promoter/operator region could be established. By way of illustration, sequences corresponding to IF-4 for other genes could then be constructed without having to reconstruct the entire 37 base pairs needed to reconstitute the trp promoter/operator and would only require bases at the 5' end such as would facilitate insertion in the proper reading frame with the complete promoter/operator.

Consistent with this goal, sequence IF-4 was reconstructed to incorporate an XbaI restriction site 3' to the base pairs completing the trp promoter/operator. The construction is shown in Table V below.

TABLE V

```
HpaI
       ┌────────── a ──────────┬────────── c ──┐
       AA CTA GTA CGC AAG TTC ACG TAA AAA GGG
       TT GAT CAT GCG TTC AAG TGC ATT TTT CCC
       └──────────── b ─────────┘

XbaI         -1  1   2   3   4       BamHI
                    Met Cys Tyr Cys Gln
       ┌──────────────────── e ────────────────┐
       TAT│CTA GAA ATG TGT TAC TGC CAG
       ATA GAT C│TT TAC ACA ATG ACG GTC CTAG
       └── d ──┘└──────────── f ───────────────┘
```

This variant form of segment IF-4 was inserted in pINTγ-trpI7 (digested with HpaI and BamHI) to generate plasmid pINTγ-TXb4 from which the IFN-γ-specifying gene could be deleted by digestion with XbaI and SalI and the entire trp promoter/operator would remain on the large fragment.

The following example relates to construction of structural analogs of IFN-γ whose polypeptide structure differs from that of IFN-γ in terms of the the identity of location of one or more amino acids.

EXAMPLE 5

A first class of analogs of IFN-γ was formed which included a lysine residue at position 81 in place of asparagine. The single base sequence change needed to generate this analog was in subunit IF-2 of Table IV in segments 35 and 36. The asparagine-specifying codon, AAC, was replaced by the lysine-specifying codon, AAG. The isolated product of expression of such a modified DNA sequence [Lys$^{81}$]IFN-γ, was designated γ-10.

Another class of IFNγ analogs consists of polypeptides wherein one or more potential glycosilation sites present in the amino acid sequence are deleted. More particularly, these consist of [Arg$^{140}$]IFN-γ or [Gln$^{140}$]IFNγ wherein the polypeptide sequence fails to include one or more naturally occurring sequences, [(Asn or Gln)-(ANY)-(Ser or Thr)], which are known to provide sites for glycosilation of the polypeptide One such sequence in IFNγ spans positions 28 through 30, (Asn-Gly-Thr), another spans positions 101 through 103 (Asn-Tyr-Ser). Preparation of an analog according to the invention with a modification at positions 28–30 involved cleavage of plasmid containing all four IFN-γ subunits with BamHI and HindIII to delete subunit IF-3, followed by insertion of a variant of subunit IF-3 wherein the AAC codon for asparagine therein is replaced by the codon for glutamine, CAG. (Such replacement is effected by modification of deoxyoligonucleotide segment 37 to include CAG rather than AAC and of segment 38 to include GTC rather than TTG. See Table IV.) The isolated product of expression of such a modified DNA sequence, [Gln$^{28}$]IFN-γ, was designated γ-12. Polypeptide analogs of this type would likely not be glycosilated if expressed in yeast cells. Polypeptide analogs as so produced are not expected to differ appreciably from naturally-occurring IFNγ in terms of reactivity with antibodies to the natural form, or in duration of antiproliferative or immunomodulatory pharmacological effects, but may display enhanced potency of pharmacological activity in one or more manner.

Other classes of IFNγ analogs consists of polypeptides wherein the [Trp$^{39}$] residue is replaced by [Phe$^{39}$], and/or wherein one or more of the methionine residues at amino acid positions 48, 80, 120 and 137 are replaced by, e.g., leucine, and/or wherein cysteines at amino acid positions 1 and 3 are replaced by, e.g., serine or are completely eliminated. These last-mentioned analogs may be more easily isolated upon microbial expression because they lack the capacity for formation of intermolecular disulfide bridge formation.

Replacement of tryptophane with phenylalanine at position 39 required substitution for a TGG codon in subunit IF-3 with TTC (although TTT could also have been used), effected by modification of the deoxyoligonucleotide segment 33 (TGG to TTC) and overlapping segment 36 (TGA to TAC) used to manufacture IF-3. [Phe$^{39}$, Lys$^{81}$]IFN-γ, the isolated product of expression of such a modified DNA sequence (which also included the above-noted replacement of asparagine by lysine at position 81) was designated γ-5.

In a like manner, replacement of one or more methionines at positions 48, 80, 120, and 137, respectively, involves alteration of subunit IF-3 (with reconstruction of deoxyoligonucleotides 31, 32 and 34), subunit IF-2 (with reconstruction of deoxyoligonucleotide segments 21 and 22); and subunit IF-1 (with reconstruction of deoxyoligonucleotide segments 7 and 10 and/or 3 and 4). An analog of IFN-γ wherein threonine replaced methionine at position 48 was obtained by modification of segment 31 in subunit IF-3 to delete the methionine-specifying codon ATG and replace it with an ACT codon. Alterations in segments 34 (TAC to TGA) were also needed to effect this change. (Thr$^{48}$, Lys$^{81}$] IFN-γ, the isolated product of expression of such a modified DNA sequence (also including a lysine-specifying codon at position 81) was designated γ-6.

Replacement or deletions of cysteines at positions 1 and 3 involves only alteration of subunit IF-4. As a first example, modifications in construction of subunit IF-4 to replace both of the cysteine-specifying codons at positions 1 and 3 (TGT and TGC, respectively) with the serine-specifying codon, TCT, required reconstruction of only 2 segments (see e and f of Table IV). [Ser$^1$, Ser$^3$, Lys$^{81}$]IFN-γ, the isolated product of expression of the thus modified [Lys$^{81}$]IFN-γ DNA sequence, was designated γ-2. As another example, [Lys$^1$, Lys$^2$, Gln$^3$, Lys$^{81}$]IFN-γ, designated γ-3, was obtained as an expression product of a modified construction of subunit IF-4 wherein codons AAA, AAA, and CAA respectively replaced TTG, TAC and TGC. Finally, [des-Cys$^1$, des-Tyr$^2$, des-Cys$^3$, Lys$^{81}$]IFN-γ, designated γ-4, was obtained by means of modification of subunit IF-4 sections to

5'-ATC CAG-3'

3'-TAC GTC-5' in the amino acid specifying region. It should be noted that the above modifications in the initial amino acid coding regions of the gene were greatly facilitated by the construction of pINTγ-TXb4 in Example 4 which meant that only short sequences with XbaI and BamHI sticky ends needed to be constructed to complete the amino terminal protein coding sequence, and link the gene to the complete trp promoter.

Among other classes of IFN-γ analog polypeptide provided by the present invention are those including polypeptides which differ from IFN-γ in terms of amino acids traditionally held to be involved in secondary and tertiary configuration of polypeptides. As an example, provision of a cysteine residue at an intermediate position in the IFN-γ polypeptide may generate a species of polypeptide structurally facilitative of formation of intramolecular disulfide bridges between amino terminal and intermediate cysteine residues such as found in IFN-γ. Further, insertion or deletion of prolines in polypeptides according to the invention may alter linear and bending configurations with corresponding effects on biological activity. [Lys$^{81}$, Cys$^{95}$]IFN-γ, desigated γ-9, was isolated upon expression of a DNA sequence fashioned with

5'-TCG-3'

3'-AGC-5' replacing

5'-TTC-3' 3'-AAG-5' in sections 17 and 18 of subunit IF-2. A DNA sequence specifying [Cys$^{95}$]IFN-γ (to be designated γ-11) is being constructed by the same general procedure. Likewise, a gene coding for [Cys$^{95}$, Pro$^{104}$]IFN-γ is under construction with the threonine-specifying codon ACA (section 15 of IF-2) being replaced by the proline-specifying codon CCA.

[Glu$^5$]IFN-γ, to be designated γ-13, will result from modification of section 43 in subunit IF-3 to include the glutamate codon, GAA, rather than the aspartic acid specifying codon, GAT. Because such a change would no longer permit the presence of a BamHI recognition site at that locus, subunit IF-3 will likely need to be constructed as a composite subunit with the amino acid specifying portions of subunit IF-4, leaving no restriction site between XbaI and HindIII in the assembled gene. This analog of IFN-γ is expected to be less acid labile than the naturally-occurring form.

The above analogs having the above-noted tryptophane and/or methionine and/or cysteine replacements are not expected to differ from naturally-occurring IFNγ in terms of reactivity with antibodies to the natural form or in potency of antiproliferative or immunomodulatory effect but are expected to have enhanced duration of pharmacological effects.

Still another class of analogs consists of polypeptides of a "hybrid" or "fused" type which include one or more additional amino acids at the end of the prescribed sequence. These would be expressed by DNA sequences formed by the addition, to the entire sequence coding for IFNγ, of another manufactured DNA sequence, e.g., one of the subunits coding for a sequence of polypeptides peculiar to LeIFN-Con, described infra. The polypeptide expressed is expected to retain at least some of the antibody reactivity of naturally-occurring IFNγ and to display some degree of the antibody reactivity of LeIFN. Its pharmacological activities are expected to be superior to naturally-occurring IFNγ both in terms of potency and duration of action.

Table VI, below, sets forth the results of studies of antiviral activity of IFN-γ prepared according to the invention along with that of certain of the analogs tested. Relative antiviral activity was assayed in human HeLa cells infected with encephalo-myocarditis virus (EMCV) per unit binding to a monoclonal antibody to IFN-γ as determined in an immunoabsorbant assay.

TABLE VI

| Interferon | Relative Antiviral Activity |
|---|---|
| γ-1 | 1.00 |
| γ-4 | 0.60 |
| γ-5 | 0.10 |
| γ-6 | 0.06 |
| γ-10 | 0.51 |

The following example relates to modifications in the polypeptide coding region of the DNA sequences of the previous examples which serve to enhance the expression of desired products.

EXAMPLE 6

Preliminary analyses performed on the polypeptide products of microbial expression of manufactured DNA sequences coding for IFN-γ and analogs of IFN-γ revealed that two major proteins were produced in approximately equal quantities—a 17K form corresponding to the complete 146 amino acid sequence and a 12K form corresponding to an interferon fragment missing about 50 amino acids of the amino terminal. Review of codon usage in the manufactured gene revealed the likelihood that the abbreviated species was formed as a result of microbial translation initiation at the Met$^{48}$ residue brought about by the similarity of base sequences 3' thereto to a Shine-Delgarno ribosome binding sequence. It thus appeared that while about half of the transcribed mRNA's bound to ribosomes only at a locus prior to the initial methionine, the other half were bound at a locus prior to the Met$^{48}$ codon. In order to diminish the likelihood of ribosome binding internally within the polypeptide coding region, sections 33 and 34 of subunit IF-3 were reconstructed. More specifically, the GAG codon employed to specify a glutamate residue at position 41 was replaced by the alternate, GAA, codon and the CGT codon employed to specify arginine at position 45 was replaced by the alternate, CGC, codon. These changes, effected during construction of the gene specifying the γ-6 analog of IFN-γ, resulted in the expression of a single predominant species of polypeptide of the appropriate length.

The following examples 7 and 8 relate to procedures of the invention for generating a manufactured gene specifying the F subtype of human leukocyte interferon ("LeuIFN-F" or "IFN-αF") and polypeptide analogs thereof.

EXAMPLE 7

The amino acid sequences for the human leukocyte interferon of the F subtype has been deduced by way of sequencing of cDNA clones. See, e.g., Goedell, et al., Nature, 200, pp. 20–26 (1981). The general procedures of prior Examples 1, 2 and 3 were employed in the design and assembly of a manufactured DNA sequence for use in microbial expression of IFN-αF in E. coli by means of a pBR322-derived expression vector. A general plan for the construction of three "major" subunit DNA sequences (LeuIFN-F I, LeuIFN-F II and LeuIFN-F III) and one "minor" subunit DNA sequence (LeuIFN-F IV) was evolved and is shown in Table VII below.

TABLE VII

```
LeuIFN-F IV

XbaI       -1   1                                9        BstE II
            Met Cys Asp Leu Pro Gln Thr His Ser Leu
   ┌────────43─────────┬────────────41──────────────┐
    CTAGAGA ATG TGT GAT TTA CCT CAA ACT CAT TCT CTT G
            TCT TAC ACA CTA AAT GGA GTT TGA GTA AGA GAA CCATTG
    └────────44─────────┴────────────42──────────────┘

LeuIFN-F III

EcoRI       10                                       20
            Gly Asn Arg Arg Ala Leu Ile Leu Leu Ala Gln Met Gly Arg Ile Ser Pro Phe
   ┌──────────────39──────────────┬──────────────37──────────────┐
    AATTCATTA GGT AAC CGT CGC GCT CTG ATT CTG CTG GCA CAG ATG GGT CGT ATT TCC CCG TTT
             GTAAT CCA TTG GCA GCG CGA GAC TAA GAC GAC CGT GTC TAC CCA GCA TAA AGG GGC AAA
   └──────────────40──────────────┴──────────────38──────────────┘
            BstE II 30                                    40
    Ser Cys Leu Lys Asp Arg His Asp Phe Gly Phe Pro Gln Glu Glu Phe Asp Gly Asn Gln Phe
   ┌──────────────35──────────────┬──────────────33──────────────┐
    AGC TGC CTG AAA GAC CGT CAC GAC TTC GGC TTT CCG CAA GAA GAG TTC GAT GGC AAC CAA TTC
    TCG ACG GAC TTT CTG GCA GTG CTG AAG CCG AAA GGC GTT CTT CTC AAG CTA CCG TTG GTT AAG
   └──────────────36──────────────┴──────────────34──────────────┘
```

TABLE VII-continued

```
     50                                       60
Gln Lys Ala Gln Ala Ile Ser Val Leu His Glu Met Ile Gln Gln Thr Phe Asn Leu Phe Ser
——————————31——————————      ——————29——————
CAG AAA GCT CAG GCA ATC TCT GTA CTG CAC GAA ATG ATC CAA CAG ACC TTC AAC CTG TTT TCC
GTC TTT CGA GTC CGT TAG AGA CAT GAC GTG CTT TAC TAG GTT GTC TGG AAG TTG GAC AAA AGG
——————————32——————————      ——————30——————
 70                               79
Thr Lys Asp Ser Ser Ala Thr Trp Glu Gln     Hind III
————27————————  ————25——————
ACT AAA GAC AGC TCT GCT ACC TGG GAA CAA
TGA TTT CTG TCG AGA CGA TGG ACC CTT GTT TCGA
————28————————  ————26——————
```

LeuIFN-F II

```
EcoRI      80                              90
           Ser Leu Leu Glu Lys Phe Ser Thr Glu Leu Asn Gln Gln
      ————23——————          ——————21——————
AATTCAGGCA AGC TTG CTG GAG AAG TTC TCC ACT GAA CTG AAC CAG CAG
      GTCCGT TCG AAC GAC CTC TTC AAG AGG TGA CTT GAC TTG GTC GTC
             ————24——————          ——————22——————
         Hind III
                        100
Leu Asn Asp Met Glu Ala Cys Val Ile Gln Glu Val Gly Val Glu Glu
————————19————————          ——————17——————
CTG AAC GAC ATG GAA GCA TGC GTA ATC CAG GAA GTT GGT GTA GAA GAG
GAC TTG CTG TAC CTT CGT ACG CAT TAG GTC CTT CAA CCA CAT CTT CTC
————————20————————          ——————18——————
  110        113
Thr Pro Leu Met Asn      SalI
————15—————
ACT CCG CTG ATG AAC G
TGA GGC GAC TAC TTG CAGCT
       ——————16——————
```

LeuIFN-F I

```
EcoRI    114                120                                  130
         Val Asp Ser Ile Leu Ala Val Lys Lys Tyr Phe Gln Arg Ile Thr Leu Tyr Leu
       ————13——————                    ——————11——————
AATTCAGGC GTC GAC TCT ATT CTG GCA GTT AAA AAG TAC TTC CAG CGT ATC ACT CTG TAC CTG
    GTCCG CAG CTG AGA TAA GAC CGA CAA TTT TTC ATG AAG GTC GCA TAG TGA GAC ATG GAC
              ————14——————                    ——————12——————
         Sal I
                            140                                150
Thr Glu Lys Lys Tyr Ser Pro Cys Ala Trp Glu Val Val Arg Ala Glu Ile Met Arg Ser Phe
————9————            ————7————              ————5————
ACC GAA AAG AAA TAT TCT CCG TGC GCT TGG GAA GTA GTT CGC GCT GAA ATT ATG CGT TCT TTC
TGG CTT TTC TTT ATA AGA GGC ACG CGA ACC CTT CAT CAA GCG CGA CTT TAA TAC GCA AGT AAG
————10———            ————8————              ————6————
                       160                 166           BamHI
Ser Leu Ser Lys Ile Phe Gln Glu Arg Leu Arg Arg Lys Glu Stp Stp     Sal I (end)
————————3————————                    ————1————
TCT CTG AGC AAA ATC TTC CAG GAG CGT CTG CGC CGT AAA GAA TAA TAG GATCC
AGA GAC TCG TTT TAG AAG GTC CTC GCA GAC GCG GCA TTT CTT ATT ATC CTAG GAGCT
————————4————————                    ————2————
```

As in the case of the gene manufacture strategy set out in Table IV, the strategy of Table VII involves use of bacterial preference codons wherever it is not inconsistent with deoxyribonucleotide segment constructions. Construction of an expression vector with the subunits was similar to that involved with the IFNγ-specifying gene, with minor differences in restriction enzymes employed. Subunit I is ligated into pBR322 cut with EcoRI and SalI. (Note that the subunit terminal portion includes a single stranded SalI "sticky end" but, upon complementation, a SalI recognition site is not reconstituted. A full BamHI recognition site remains, however, allowing for subsequent excision of the subunit.) This first intermediate plasmid is amplified and subunit II is inserted into the amplified plasmid after again cutting with EcoRI and SalI. The second intermediate plasmid thus formed is amplified and subunit III is inserted into the amplified plasmid cut with EcoRI and HindIII. The third intermediate plasmid thus formed is amplified. Subunit IV is ligated to an EcoRI and XbaI fragment isolated from pINTγ-TXb4 of Example 4 and this ligation product (having EcoRI and BstEII sticky ends) is then inserted into the amplified third intermediate plasmid cut with EcoRI and BstEII to yield the final expression vector.

The isolated product of trp promoter/operator controlled E. coli expression of the manufactured DNA sequence of Table VII as inserted into the final expression vector was designated IFN-αF$_1$.

EXAMPLE 8

As discussed infra with respect to consensus leukocyte interferon, those human leukocyte interferon subtypes having a threonine residue at position 14 and a methionine residue at position 16 are reputed to display greater antiviral activity than those subtypes possessing Ala$^{14}$ and Ile$^{16}$ residues. An analog of human leukocyte interferon subtype F was therefore manufactured by means of microbial expression of a DNA sequence of Example 7 which had been altered to specify threonine and methionine as residues 14 and 16, respectively. More specifically, [Thr$^{14}$, Met$^{16}$] IFN-αF, designated IFN-αF$_2$, was expressed in E.coli upon transformation with a vector of Example 7 which had been cut with SalI and HindIII and into which a modified subunit II (of Table VII) was inserted. The specific modifications of subunit II involved assembly with segment 39 altered to replace the alanine-specifying codon, GCT, with a threonine-specifying ACT codon and replace the isoleucine-specifying codon, ATT, with an ATG codon. Corresponding changes in complementary bases were made in section 40 of subunit LeuIFN-FII.

The following Examples 9 and 10 relate to practice of the invention in the microbial synthesis of consensus human leukocyte interferon polypeptides which can be designated as analogs of human leukocyte interferon subtype F.

EXAMPLE 9

"Consensus human leukocyte interferon" ("IFN-Con," "LeuIFN-Con") as employed herein shall mean a non-naturally-occurring polypeptide which predominantly includes those amino acid residues which are common to all naturally-occurring human leukocyte interferon subtype sequences and which includes, at one or more of those positions wherein there is no amino acid common to all subtypes, an amino acid which predominantly occurs at that position and in no event includes any amino acid residue which is not extant in that position in at least one naturally-occurring subtype. (For purposes of this definition, subtype A is positionally aligned with other subtypes and thus reveals a "missing" amino acid at position 44.) As so defined, a consensus human leukocyte interferon will ordinarily include all known common amino acid residues of all subtypes. It will be understood that the state of knowledge concerning naturally-occurring subtype sequences is continuously developing. New subtypes may be discovered which may destroy the "commonality" of a particular residue at a particular position. Polypeptides whose structures are predicted on the basis of a later-amended determination of commonality at one or more positions would remain within the definition because they would nonetheless predominantly include common amino acids and because those amino acids no longer held to be common would nonetheless quite likely represent the predominant amino acid at the given positions. Failure of a polypeptide to include either a common or predominant amino acid at any given position would not remove the molecule from the definition so long as the residue at the position occurred in at least one subtype. Polypeptides lacking one or more internal or terminal residues of consensus human leukocyte interferon or including internal or terminal residues having no counterpart in any subtype would be considered analogs of human consensus leukocyte interferon.

Published predicted amino acid sequences for eight cDNA-derived human leukocyte interferon subtypes were analyzed in the context of the identities of amino acids within the sequence of 166 residues. See, generally, Goedell, et al., Nature, 290, pp. 20–26 (1981) comparing LeIFN-A through LeIFN-H and noting that only 79 amino acids appear in identical positions in all eight interferon forms and 99 amino acids appear in identical positions if the E subtype (deduced from a cDNA pseudogene) was ignored. Each of the remaining positions was analyzed for the relative frequency of occurrence of a given amino acid and, where a given amino acid appeared at the same position in at least five of the eight forms, it was designated as the predominant amino acid for that position. A "consensus" polypeptide sequence of 166 amino acids was plotted out and compared back to the eight individual sequences, resulting in the determination that LeIFN-F required few modifications from its "naturally-occurring" form to comply with the consensus sequence.

A program for construction of a manufactured IFN-Con DNA sequence was developed and is set out below in Table VIII. In the table, an asterisk designates the variations in IFN-αF needed to develop LeIFN-Con$_1$, i.e., to develop the [Arg$^{22}$, Ala$^{76}$, Asp$^{78}$, Glu$^{79}$, Tyr$^{86}$, Tyr$^{90}$, Leu$^{96}$, Thr$^{156}$, Asn$^{157}$, Leu$^{158}$] analog of IFN-αF. The illustrated top strand sequence includes, wherever possible, codons noted to the subject of preferential expression in E. coli. The sequence also includes bases providing recognition sites for Sal, HindIII, and BstE2 at positions intermediate the sequence and for XBaI and BamHI at its ends. The latter sites are selected for use in incorporation of the sequence in a pBR322 vector, as was the case with the sequence developed for IFN-αF and its analogs.

TABLE VIII

```
-1  1                                           10
Met-Cys-Asp-Leu-Pro-Gln-Thr-His-Ser-Leu-Gly-Asn-
ATG TGT GAT TTA CCT CAA ACT CAT TCT CTT GGT AAC

20       *
Arg-Arg-Ala-Leu-Ile-Leu-Leu-Ala-Gln-Met-Arg-Arg-
CGT CGC GCT CTG ATT CTG CTG GCA CAG ATG CGT CGT

30
Ile-Ser-Pro-Phe-Ser-Cys-Leu-Lys-Asp-Arg-His-Asp-
ATT TCC CCG TTT AGC TGC CTG AAA GAC CGT CAC GAC

40
Phe-Gly-Phe-Pro-Gln-Glu-Glu-Phe-Asp-Gly-Asn-Gln-
TTC GGC TTT CCG CAA GAA GAG TTC GAT GGC AAC CAA

50
Phe-Gln-Lys-Ala-Gln-Ala-Ile-Ser-Val-Leu-His-Glu-
TTC CAG AAA GCT CAG GCA ATC TCT GTA CTG CAC GAA 60                                              70
Met-Ile-Gln-Gln-Thr-Phe-Asn-Leu-Phe-Ser-Thr-Lys-
ATG ATC CAA CAG ACC TTC AAC CTG TTT TCC ACT AAA

*      *    *   80
Asp-Ser-Ser-Ala-Ala-Trp-Asp-Glu-Ser-Leu-Leu-Glu-
GAC AGC TCT GCT GCT TGG GAC GAA AGC TTG CTG GAG

*            *90
Lys-Phe-Tyr-Thr-Glu-Leu-Tyr-Gln-Gln-Leu-Asn-Asp-
AAG TTC TAC ACT GAA CTG TAT CAG CAG CTG AAC GAC

*                100
```

TABLE VIII-continued

```
Leu-Glu-Ala-Cys-Val-Ile-Gln-Glu-Val-Gly-Val-Glu-
CTG GAA GCA TGC GTA ATC CAG GAA GTT GGT GTA GAA

110
Glu-Thr-Pro-Leu-Met-Asn-Val-Asp-Ser-Ile-Leu-Ala-
GAG ACT CCG CTG ATG AAC GTC GAC TCT ATT CTG GCA 120                                      130
Val-Lys-Lys-Tyr-Phe-Gln-Arg-Ile-Thr-Leu-Tyr-Leu-
GTT AAA AAG TAC TTC CAG CGT ATC ACT CTG TAC CTG

140
Thr-Glu-Lys-Lys-Tyr-Ser-Pro-Cys-Ala-Trp-Glu-Val-
ACC GAA AAG AAA TAT TCT CCG TGC GCT TGG GAA GTA

150
Val-Arg-Ala-Glu-Ile-Met-Arg-Ser-Phe-Ser-Leu-Ser-
GTT CGC GCT GAA ATT ATG CGT TCT TTC TCT CTG TCT
```

TABLE VIII-continued

```
 *   *   *            160                        166 Stop
Thr-Asn-Leu-Gln-Glu-Arg-Leu-Arg-Arg-Lys-Glu
ACT AAC CTG CAG GAG CGT CTG CGC CGT AAA GAA TAA Stop

TAG
```

Table IX below sets out the specific double stranded DNA sequence for preparation 4 subunit DNA sequences for use in manufacture of IFN-Con$_1$. Subunit LeuIFN-Con IV is a duplicate of LeuIFN-F IV of Table VIII. Segments of subunits which differ from those employed to construct the IFN-αF gene are designated with a "prime" (e.g., 37' and 38' are altered forms of sections 37 and 38 needed to provide arginine rather than glycine at position 22).

TABLE IX

```
LeuIFN Con IV

XbaI    -1   1   2   3   4   5   6   7   8   9        BstE II
             Met Cys Asp Leu Pro Gln Thr His Ser Leu

————43————————    ————————41——————————
     CTAGAGA ATG TGT GAT TTA CCT CAA ACT CAT TCT CTT G
             TCT TAC ACA CTA AAT GGA GTT TGA GTA AGA GAA CCATTG
             ————44————————    ————————42——————————

LeuIFN Con III

EcoRI      10                                      20
          Gly Asn Arg Arg Ala Leu Ile Leu Leu Ala Gln Met Arg Arg Ile Ser Pro Phe

——————————39——————————    ——————————37'——————————
    AATTCATTA GGT AAC CGT CGC GCT CTG ATT CTG CTG GCA CAG ATG CGT CGT ATT TCC CCG TTT
             GTAAT CCA TTG GCA GCG CGA GAC TAA GAC GAC CGT GTC TAC GCA GCA TAA AGG GGC AAA
                          ——————————40——————————    ——————————38'——————————
              BstE II
           30                                          40
Ser Cys Leu Lys Asp Arg His Asp Phe Gly Phe Pro Gln Glu Glu Phe Asp Gly Asn Gln Phe
   ——————————35——————————    ——————————33——————————
AGC TGC CTG AAA GAC CGT CAC GAC TTC GGC TTT CCG CAA GAA GAG TTC GAT GGC  AAC CAA TTC
TCG ACG GAC TTT CTG GCA GTG CTG AAG CCG AAA GGC GTT CTT CTC AAG CTA CCG' TTG GTT AAG
   ——————————36——————————    ——————————34——————————
       50                                        60
Gln Lys Ala Gln Ala Ile Ser Val Leu His Glu Met Ile Gln Gln Thr Phe Asn Leu Phe Ser
   ——————————31——————————    ——————————29——————————
CAG AAA GCT CAG GCA ATC TCT GTA CTG CAC GAA ATG ATC CAA CAG ACC TTC AAC CTG TTT TCC
GTC TTT CGA GTC CGT TAG AGA CAT GAC GTG CTT TAC TAG GTT GTC TGG AAG TTG GAC AAA AGG
   ——————————32——————————    ——————————30——————————
  70                              79   Hind III
Thr Lys Asp Ser Ser Ala Ala Trp Asp Glu ————27————    ————25'————
ACT AAA GAC AGC TCT GCT GCT TGG GAC GAA
TGA TTT CTG TCG AGA CGA CGA ACC CTG CTT TCGA
    ————28————    ————26'————

LeuIFN Con II

EcoRI       80                                 90
           Ser Leu Leu Glu Lys Phe Tyr Thr Glu Leu Tyr Gln Gln

————23————    ————21'————
    AATTCAGGCA AGC TTG CTG GAG AAG TTC TAC ACC GAG CTG TAT CAG CAG
               GTCCGT TCG AAC GAC CTC TTC AAG ATG TGG CTC GAC ATA GTC GTC
               ————24————    ————22'————
          Hind III
```

TABLE IX-continued

```
                            100
Leu Asn Asp Leu Glu Ala Cys Val Ile Gln Glu Val Gly Val Glu Glu
        19'                       17
CTG AAG GAC CTG GAA GCA TGC GTA ATC CAG GAA GTT GGT GTA GAA GAG
GAC TTG CTG GAC CTT CGT ACG CAT TAG GTC CTT CAA CCA CAT CTT CTC
        20'                           18
    110         113    Sal I
Thr Pro Leu Met Asn
       15
ACT CCG CTG ATG AAC G
TGA GGC GAC TAC TTG CAGCT
               16

LeuIFN Con I

EcoRI   114                 120                             130
        Val Asp Ser Ile Leu Ala Val Lys Lys Tyr Phe Gln Arg Ile Thr Leu Tyr Leu
                 13                          11
AATTCAGGC GTC GAC TCT ATT CTG GCA GTT AAA AAG TAC TTC CAG CGT ATC ACT CTG TAC CTG
         GTCCG CAG CTG AGA TAA GAC CGT CAA TTT TTC ATG AAG GTC GCA TAG TGA GAC ATG GAC
                       14                                           12
        Sal I
                        140                             150
Thr Glu Lys Lys Tyr Ser Pro Cys Ala Trp Glu Val Val Arg Ala Glu Ile Met Arg Ser Phe
      9                           7                         5
ACC GAA AAG AAA TAT TCT CCG TGC GCT TGG GAA GTA GTT CGC GCT GAA ATT ATG CGT TCT TTC
TGG CTT TTC TTT ATA AGA GGC ACG CGA ACC CTT CAT CAA GCG CGA CTT TAA TAC GCA AGA AAG
          10                          8                              6
                      160               166      BamHI
Ser Leu Ser Thr Asn Leu Gln Glu Arg Leu Arg Arg Lys Glu Stp Stp    Sal I (end)
              3'                              1
TCT CTG AGC ACT AAC CTG CAG GAG CGT CTG CGC CGT AAA GAA TAA TAG GATCC
AGA GAC TCG TGA TTG GAC GTC CTC GCA GAC GCG GCA TTT CTT ATT ATC CTAGGAGCT
                          4'                       2
```

The four subunits of Table IX were sequentially inserted into an expression vector according to the procedure of Example 7 to yield a vector having the coding region of Table VIII under control of a trp promoter/operator. The product of expression of this vector in *E. coli* was designated IFN-Con$_1$. It will be noted that this polypeptide includes all common residues indicated in Goedell, et al., supra, and, with the exception of Ser$^{80}$, Glu$^{83}$, Val$^{114}$, and Lys$^{121}$, included the predominant amino acid indicated by analysis of the reference's summary of sequences. The four above-noted residues were retained from the native IFN-αF sequence to facilitate construction of subunits and assembly of subunits into an expression vector. (Note, e.g., serine was retained at position 80 to allow for construction of a HindIII site.)

Since publication of the Goedell, et al. summary of IFN-α subtypes, a number of additional subtypes have been ascertained. FIGS. 2A–2C set out in tabular form the deduced sequences of the 13 presently known subtypes (exclusive of those revealed by five known cDNA pseudogenes) with designations of the same IFN-α subtypes from different laboratories indicated parenthetically (e.g., IFN-α6 and IFN-αK). See, e.g., Goedell, et al., supra; Stebbing, et al., in: Recombinant DNA Products, Insulin, Interferons and Growth Hormones (A. Bollon, ed.), CRC Press (1983); and Weissman, et al., U.C.L.A. Symp. Mol. Cell. Biol., 25, pp. 295–326 (1982). Positions where there is no common amino acid are shown in bold face. IFN-α subtypes are roughly grouped on the basis of amino acid residues. In seven positions (14, 16, 71, 78, 79, 83, and 160) the various subtypes show just two alternative amino acids, allowing classification of the subtypes into two subgroups (I and II) based on which of the seven positions are occupied by the same amino acid residues. Three IFN-α subtypes (H, F, and B) cannot be classified as Group I or Group II and, in terms of distinguishing positions, they appear to be natural hybrids of both group subtypes. It has been reported that IFN-α subtypes of the Group I type display relatively high antiviral activity while those of Group II display relatively high antitumor activity.

IFN-Con$_1$ structure is described in the final line of the FIGS. 2A–2C. It is noteworthy that certain residues of IFN-Con$_1$ (e.g., serine at position 8) which were determined to be "common" on the basis of the Goedell, et al., sequences are now seen to be "predominant." Further, certain of the IFN-Con$_1$ residues determined to be predominant on the basis of the reference (Arg$^{22}$, Asp$^{78}$, Glu$^{79}$, and Tyr86) are no longer so on the basis of updated information, while certain heretofore nonpredominant others (Ser$^{80}$ and Glu$^{83}$) now can be determined to be predominant.

EXAMPLE 10

A human consensus leukocyte interferon which differed from IFN-Con$_1$ in terms of the identity of amino acid residues at positions 14 and 16 was prepared by modification of the DNA sequence coding for IFN-Con$_1$. More specifically, the expression vector for IFN-Con$_1$ was treated with BstEII and Hind III to delete subunit LeuIFN Con III. A modified subunit was inserted wherein the alanine-specifying codon, GCT, of sections 39 and 40 was altered to a threonine-specifying codon, ACT, and the isoleucine codon, CTG, was changed to ATG. The product of expression of the modified manufactured gene, [Thr[14], Met[16], Arg[22], Ala[76], Asp[78], Glu[79], Tyr[86], Tyr[90], Leu[96], Thr[156], Asn[157], Leu[158]]IFN-αF, was designated IFN-Con$_2$.

Presently being constructed is a gene for a consensus human leukocyte interferon polypeptide which will differ from IFN-Con$_1$ in terms of the identity of residues at positions 114 and 121. More specifically, the Val[114] and Lys[121] residues which duplicate IFN-αF subtype residues but are not predominant amino acids will be changed to the predominant Glu[114] and Arg[121] residues, respectively. Because the codon change from Val[114] to Arg[114] (e.g., GTC to GAA) will no longer allow for a SalI site at the terminal portion of subunit LeuIFN Con I (of Table IX), subunits I and II will likely need to be constructed as a single subunit. Changing the AAA, lysine, codon of sections 11 and 12 to CTG will allow for the presence of arginine at position 121. The product of microbial expression of the manufactured gene, [Arg[22], Ala[76], Asp[78], Glu[79], Tyr[86], Tyr[90], Le[96], Glu[114], Arg[121], Thr[156], Asn[157], Leu[158]] IFN-αF, will be designated IFN-Con$_3$.

The following example relates to procedures for enhancing levels of expression of exogenous genes in bacterial species, especially, *E.coli*.

EXAMPLE 11

In the course of development of expression vectors in the above examples, the trp promoter/operator DNA sequence was employed which included a ribosome binding site ("RBS") sequence in a position just prior to the initial translation start (Met$^{-1}$, ATG). An attempt was made to increase levels of expression of the various exogenous genes in *E.coli* by incorporating DNA sequences duplicative of portions of putative RBS sequences extant in genomic *E.coli* DNA sequences associated with highly expressed cellular proteins. Ribosome binding site sequences of such protein-coding genes as reported in Inokuchi, et al. *Nuc. Acids. Res.*, 10, pp. 6957–6968 (1982), Gold, et al.,*Ann. Rev. Microbiol.*, 35, pp. 365–403 (1981) and Alton, et al., *Nature,* 282, pp. 864–869 (1979), were reviewed and the determination was made to employ sequences partially duplicative of those associated with the *E.coli* proteins OMP-F (outer membrane protein F), CRO and CAM (chloramphenicol transacetylase).

By way of example, to duplicate a portion of the OMP-F RBS sequence the following sequence is inserted prior to the Met$^{-1}$ codon.

5'-AACCATGAGGGTAATAAATA-3'

3'-TTGGTACTCCCATTATTTAT-5'

In order to incorporate this sequence in a position prior to the protein coding region of, e.g., the manufactured gene coding for IFN-Con$_1$ or IFN-αF$_1$, subunit IV of the expression vector was deleted (by cutting the vector with XbaI and BstEII) and replaced with a modified subunit IV involving altered sections 41A and 42A and the replacement of sections 43 and 44 with new segments RB1 and RB2. The construction of the modified sequence is as set out in Table X, below.

TABLE X

```
XbaI                                    -1   1    2
                                        Met  Cys  Asp
  ┌─────────RB1─────────────┐
  CTAGAAA CCA TGA GGG TAA TAA ATA ATG TGT GAT
      TTT GGT ACT CCC ATT ATT TAT TAC ACA CTA
      └──────────RB2────────┘

3    4    5    6    7    8    9
  Leu  Pro  Gln  Thr  His  Ser  Leu     BstEII

┌────41A──────────────────┐
  TTA CCT CAA ACT CAT TCT CTT G
  AAT GGA GTT TGA GTA AGA GAA CATG
  └──────42A────────────────┘
```

Table XI, below, illustrates the entire DNA sequence in the region preceding the protein coding region of the reconstructed gene starting with the HpaI site within the trp promoter/operator (compare subunit IF-4 of Table IV).

TABLE XI

```
HpaI                                              XbaI
AAC TAG TAC GCA AGT TCA CGT AAA AAG GGT ATC TAG
TTG ATC ATG CGT TCA AGT GCA TTT TTC CCA TAG ATC

-1   1    2    3    4
                              Met  Cys  Asp  Leu  Pro
AAA CCA TGA GGG TAA TAA ATA ATG TGT GAT TTA CCT
TTT GGT ACT CCC ATT ATT TAT TAC ACA CTA AAT GGA 5    6    7    8    9
Gln  Thr  His  Ser  Leu    BstE II
CAA ACT CAT TCT CTT G
GTT TGA GTA AGA GAA CATG
```

Similar procedures were followed to incorporate sequences duplicative of RBS sequences of CRO and CAM genes, resulting in the following sequences immediately preceding the Met$^{-1}$ codon.

```
               1         10         20
CRO:           GCATGTACTAAGGAGGTTGT
               CGTACATGATTCCTCCAACA 1         10         20
CAM:           CAGGAGCTAAGGAAGCTAAA
               GTCCTCGATTCCTTCGATTT
```

It will be noted that all the RBS sequence inserts possess substantial homology to Shine-Delgarno sequences, are rich in adenine and include sequences ordinarily providing "stop" codons.

Levels of *E.coli* expression of IFN-Con$_1$ were determined using trp-controlled expression vectors incorporating the three RBS inserts (in addition to the RES sequence extant in the complete trp promoter/operator). Expression of the desired polypeptide using the OMP-F RBS duplicating sequence was at from 150–300 mg per liter of culture, representing from 10 to 20 percent of total protein. Vectors incorporating the CAM RBS duplicating sequence provided levels of expression which were about one-half that provided by the OMP-F variant. Vectors including the CRO RBS duplicating sequence yielded the desired protein at levels of about one-tenth that of the OMP-F variant.

The following example relates to antiviral activity screening of human leukocyte interferon and polypeptides provided by the preceding examples.

EXAMPLE 12

Table XII below provides the results of testing of antiviral activity in various cell lines of natural (buffy coat) interferon and isolated, microbially-expressed, polypeptides designated IFN-$\alpha F_1$, IFN-$\alpha F_2$, IFN-$Con_1$, and IFN-$Con_2$. Viruses used were VSV (vesicular stomatitis virus) and EMCV (encephalomyocarditis virus). Cell lines were from various mammalian sources, including human (WISH, HeLa), bovine (MDBK), mouse (MLV-6), and monkey (Vero). Antiviral activity was determined by an end-point cytopathic effect assay as described in Weck, et al., *J. Gen. Virol.*, 57, pp. 233–237 (1981) and Campbell, et al., *Can. J. Microbiol.*, 21, pp. 1247–1253 (1975). Data shown was normalized for antiviral activity in WISH cells.

TABLE XII

| Virus | Cell Line | Buffy Coat | IFN-$\alpha F_1$ | IFN-$\alpha F_2$ | IFN-$Con_1$ | IFN-$Con_2$ |
|---|---|---|---|---|---|---|
| VSV | WISH | 100 | 100 | 100 | 100 | 100 |
| VSV | HeLa | 400 | 100 | ND* | 200 | 100 |
| VSV | MDBK | 1600 | 33 | ND | 200 | 300 |
| VSV | MLV-6 | 20 | 5 | ND | 3 | 20 |
| VSV | Vero | 10 | 0.1 | ND | 10 | 0.1 |
| EMCV | WISH | 100 | 100 | 100 | 100 | 100 |
| EMCV | HeLa | 100 | 5 | ND | 33 | 33 |
| EMCV | Vero | 100 | 20 | ND | 1000 | 10 |

*ND—no data presently available.

It will be apparent from the above examples that the present invention provides, for the first time, an entire new genus of synthesized, biologically active proteinaceous products which products differ from naturally-occurring forms in terms of the identity and/or location of one or more amino acids and in terms of one or more biological (e.g., antibody reactivity) and pharmacological (e.g., potency or duration of effect) but which substantially retain other such properties.

Products of the present invention and/or anti-bodies thereto may be suitably "tagged", for example radiolabelled (e.g., with $I^{125}$) conjugated with enzymes or fluorescently labelled, to provide reagent materials useful in assays and/or diagnostic test kits, for the qualitative and/or quantitative determination of the presence of such products and/or said antibodies in fluid samples. Such anitbodies may be obtained from the innoculation of one or more animal species (e.g., mice rabbit, goat, human, etc.) or from monoclonal anti-body sources. Any of such reagent materials may be used alone or in combination with a suitable substrate, e.g., coated on a glass or plastic particle bead.

Numerous modifications and variations in the practice of the invention are expected to occur to those skilled in the art upon consideration of the foregoing illustrative examples. Consequently, the invention should be considered as limited only to the extent reflected by the appended claims.

What is claimed is:

1. A human gamma interferon analog polypeptide having substantially the activity of human gamma interferon, said analog polypeptide being the expression product of a DNA sequence wherein the codons encoding the $Cys^1$, $Tyr^2$, and $Cys^3$ amino acid residues of human gamma interferon are deleted and replaced with a codon encoding a $Met^{-1}$ amino acid residue.

2. The analog polypeptide of claim 1 that is [$Met^{-1}$, des-$Cys^1$, des-$Tyr^2$, des-$Cys^3$]IFN-$\gamma$.

3. The analog polypeptide of claim 1 that is [$Met^{-1}$, des-$Cys^1$, des-$Tyr^2$, des-$Cys^3$, $Lys^{81}$]IFN-$\gamma$.

* * * * *

UNITED STATES PATENT AND TRADEMARK OFFICE
CERTIFICATE OF CORRECTION

PATENT NO. : 6,936,695 B1
APPLICATION NO. : 08/462022
DATED : August 30, 2005
INVENTOR(S) : Norman K. Alton et al.

It is certified that error appears in the above-identified patent and that said Letters Patent is hereby corrected as shown below:

On the Title Page
Item -54-, please delete "MANUFACTURE AND EXPRESSION OF LARGE STRUCTURAL GENES" and insert --HUMAN GAMMA INTERFERON ANALOGS--.

Item -73- on the Title Page
At field (73), please delete "Intermune" and insert --InterMune--.

Item (*) on the Title Page
At field (*), please insert --This patent is subject to a terminal disclaimer--.

At Column 1, lines 1-2, please delete "MANUFACTURE AND EXPRESSION OF LARGE STRUCTURAL GENES" and insert --HUMAN GAMMA INTERFERON ANALOGS--.

At Column 2, line 46, please delete "manis" and insert --Manis--.

At Column 2, line 49, please insert --the ready availability of "restriction endonuclease"-- before "enzymes."

At Column 5, lines 53-54, please delete "deoxyolidonucleotides" and insert --deoxyoligonucleotides--.

At Column 12, line 41, please delete "Table II and II" and insert --Tables II and III--.

At Column 13, line 56, please delete "Endonucleases-" and insert --Endonucleases--.

At Column 19, IF-1, line 2 of nucleotides, $8^{th}$ codon, please delete "CGA" and insert --GCA--.

At Column 21, line 47, please delete "sing" and insert --using--.

At Column 21, line 57, please delete "acetonitile" and insert --acetonitrile--.

At Column 22, line 38, please delete "18 he" and insert --18mM--.

At Column 22, line 44, please delete "purifier" and insert --purified--.

At Column 22, line 59, please delete "IP-2" and insert --IF-2--.

UNITED STATES PATENT AND TRADEMARK OFFICE
CERTIFICATE OF CORRECTION

PATENT NO. : 6,936,695 B1
APPLICATION NO. : 08/462022
DATED : August 30, 2005
INVENTOR(S) : Norman K. Alton et al.

It is certified that error appears in the above-identified patent and that said Letters Patent is hereby corrected as shown below:

At Column 24, line 38, please delete "glycosilation" and insert --glycosylation--.

At Column 24, line 43, please delete "glycosilation" and insert --glycosylation--.

At Column 24, line 44, please delete "polypeptide" and insert --polypeptide.--.

At Column 24, line 58, please delete "glycosilated" and insert --glycosylated--.

At Column 26, line 4, please delete" IFN-γ" and insert --IFN-α--.

At Column 37, line 20, please delete "Le$^{96}$" and insert --Leu$^{96}$--.

At Column 38, line 55, please delete "RES sequence" and insert --RBS sequence--.

At Column 40, line 10, please delete "anitbodies" and insert --antibodies--.

At Column 40, line 12, please delete "mice rabbit" and insert --mice, rabbit--.

Signed and Sealed this

Fifteenth Day of April, 2008

JON W. DUDAS
*Director of the United States Patent and Trademark Office*